(12) United States Patent
Vega Romero et al.

(10) Patent No.: US 12,183,008 B2
(45) Date of Patent: Dec. 31, 2024

(54) DEVICE AGNOSTIC SYSTEMS AND METHODS FOR ACQUIRING AND ANALYZING IMAGES FROM AN ULTRASOUND PROBE

(71) Applicant: Exo Imaging, Inc., Santa Clara, CA (US)

(72) Inventors: Roberto Ivan Vega Romero, Edmonton (CA); Seyed Ehsan Seyed Bolouri, Burnaby (CA); Amirhosein Forouzandehmoghadam, Vancouver (CA); Amir Safarpoor Kordbacheh, North Vancouver (CA); Mahdiar Nekoui, Edmonton (CA); Masood Dehghan, Edmonton (CA); Dornoosh Zonoobi, Edmonton (CA)

(73) Assignee: Exo Imaging, Inc., Santa Clara, CA (US)

( * ) Notice: Subject to any disclaimer, the term of this patent is extended or adjusted under 35 U.S.C. 154(b) by 105 days.

(21) Appl. No.: 18/168,402

(22) Filed: Feb. 13, 2023

(65) Prior Publication Data

US 2024/0273726 A1     Aug. 15, 2024

(51) Int. Cl.
*G06T 7/00*        (2017.01)
*A61B 8/00*        (2006.01)
(Continued)

(52) U.S. Cl.
CPC ............ *G06T 7/0016* (2013.01); *A61B 8/085* (2013.01); *A61B 8/4477* (2013.01); *A61B 8/461* (2013.01);
(Continued)

(58) Field of Classification Search
CPC ....... G06T 7/0016; G06T 3/4046; G06T 7/11; G06T 7/174; G06T 2207/10132;
(Continued)

(56) References Cited

U.S. PATENT DOCUMENTS

| 7,616,799 B2 | 11/2009 | Ramamurthy et al. |
| 8,280,482 B2 | 10/2012 | Rusinek et al. |

(Continued)

FOREIGN PATENT DOCUMENTS

| CA | 3032980 A1 | 7/2020 |
| CA | 3054490 A1 | 2/2021 |

(Continued)

OTHER PUBLICATIONS

Brattain et al., "Machine Learning for Medical Ultrasound: Status, Methods, and Future Opportunities", Abdominal Radiology, New York, NY, vol. 43, Feb. 28, 2018, 14 pgs.

(Continued)

*Primary Examiner* — Bo Joseph Peng
(74) *Attorney, Agent, or Firm* — Morgan, Lewis & Bockius LLP

(57) ABSTRACT

A method includes obtaining a first frame of a probed region acquired using a first probe device at a first time, and a first set of control parameters used to acquire the first frame. Processing the first frame includes segmenting features from the first frame after first probe-specific effects are reduced in the first frame based on the first set of control parameters. The method includes, when the first frame contains a respective attribute present in a second frame acquired at a time earlier than the first time using a second set of control parameters, displaying information related to differences in the respective attribute in the first frame and the second frame. The second frame is obtained by processing the one or more features segmented from the second frame after one or more second probe-specific effects are reduced in the second frame.

20 Claims, 17 Drawing Sheets

(51) Int. Cl.
  *A61B 8/08* (2006.01)
  *G06T 3/4046* (2024.01)
  *G06T 7/11* (2017.01)
  *G06T 7/174* (2017.01)

(52) U.S. Cl.
  CPC .......... *A61B 8/5207* (2013.01); *A61B 8/5269* (2013.01); *A61B 8/54* (2013.01); *G06T 3/4046* (2013.01); *G06T 7/11* (2017.01); *G06T 7/174* (2017.01); *G06T 2207/10132* (2013.01); *G06T 2207/20081* (2013.01); *G06T 2207/20084* (2013.01); *G06T 2207/20224* (2013.01)

(58) Field of Classification Search
  CPC . G06T 2207/20081; G06T 2207/20084; G06T 2207/20224; A61B 8/085; A61B 8/4477; A61B 8/461; A61B 8/5207; A61B 8/5269; A61B 8/54
  See application file for complete search history.

(56) References Cited

U.S. PATENT DOCUMENTS

| | | | |
|---|---|---|---|
| 8,355,552 | B2 | 1/2013 | Schwartz et al. |
| 8,891,881 | B2 | 11/2014 | Gupta et al. |
| 10,140,710 | B2 | 11/2018 | Kreeger |
| 10,456,113 | B2 * | 10/2019 | Moshavegh ............ A61B 8/06 |
| 10,515,452 | B2 | 12/2019 | Snook et al. |
| 10,959,702 | B2 | 3/2021 | Nouri et al. |
| 11,094,138 | B2 | 8/2021 | Canfield et al. |
| 11,160,510 | B2 | 11/2021 | Cadieu et al. |
| 2015/0334398 | A1* | 11/2015 | Socek .................. H04N 19/182 375/240.26 |
| 2017/0290567 | A1 | 10/2017 | Fujita |
| 2017/0360412 | A1* | 12/2017 | Rothberg ............ A61B 8/5207 |
| 2017/0367685 | A1* | 12/2017 | Zou ..................... G06F 18/22 |
| 2018/0021024 | A1* | 1/2018 | Fukuda ................ G06T 11/206 382/131 |
| 2018/0153505 | A1 | 6/2018 | Cadieu et al. |
| 2019/0188855 | A1* | 6/2019 | Mendes Rodrigues ... G06T 7/11 |
| 2019/0254629 | A1* | 8/2019 | Li ........................ A61B 8/463 |
| 2019/0261956 | A1 | 8/2019 | Srinivasan et al. |
| 2019/0392577 | A1 | 12/2019 | Cadieu et al. |
| 2020/0023203 | A1 | 1/2020 | Lachaine et al. |
| 2020/0060658 | A1 | 2/2020 | Gafner et al. |
| 2020/0196993 | A1 | 6/2020 | Ralston et al. |
| 2020/0211174 | A1 | 7/2020 | Rothberg et al. |
| 2020/0305837 | A1* | 10/2020 | Aladahalli ............ A61B 8/469 |
| 2021/0052255 | A1 | 2/2021 | Cadieu et al. |
| 2021/0077068 | A1 | 3/2021 | Lu et al. |
| 2021/0093298 | A1 | 4/2021 | Lovchinksy et al. |
| 2021/0100526 | A1* | 4/2021 | Schein .................. G06T 7/251 |
| 2021/0106314 | A1* | 4/2021 | Aladahalli ............ G06V 10/26 |
| 2021/0275145 | A1 | 9/2021 | De Jonge et al. |
| 2022/0008041 | A1 | 1/2022 | Pourtahmasi Roshandeh et al. |
| 2022/0160332 | A1 | 5/2022 | Schlenger et al. |

FOREIGN PATENT DOCUMENTS

| | | |
|---|---|---|
| CN | 112767355 A | 5/2021 |
| JP | 5975803 B2 | 8/2016 |
| WO | WO 2021/075418 A1 | 4/2021 |
| WO | WO2023/287705 A1 | 1/2023 |

OTHER PUBLICATIONS

Exo Imaging, Inc., International Search Report and Written Opinion, PCT/US2023/062765, Jul. 5, 2023, 16 pgs.

Stec et al., "A Systematic Review of Fatigue in Radiology: Is It a Problem?", American Journal of Roentgenology, 210(4),799-806, Apr. 2018, 8 pgs.

Tessler et al. "ACR Thyroid Imaging, Reporting and Data System (TI-RADS): White Paper of the ACR TI-RADS Committee", Journal of the American College of Radiology, vol. 14, 2017, 9 pgs.

Exo Imaging, Inc., PCT/US2024/020776, International Search Report and Written Opinion, Aug. 14, 2024, 13 pgs.

Miao, "Prior Knowledge-Guided Attention in Self-Supervised Vision Transformers", arXiv, Sep. 7, 2022, 13 pgs. retrieved on [Jun. 20, 2024]. Retrieved from the internet <URL: https://arxi v.org/abs/2209.03745> entire document.

Huang et al. "A Robust Graph-Based Segmentation Method for Breast Tumors in Ultrasound Images", Ultrasonics 52(2), Aug. 2011, 10 pgs. retrieved on [Jun. 20, 2024]. Retrieved from the internet <URL: haps://www.researchgate.net/publication/51650119_A_robust_graph-based_segmentation_method_for_breast_tumors_in_ultrasound_images> entire document.

* cited by examiner

1300

1302 Obtain a first frame of a probed region acquired using a first probe device, and a first set of control parameters used to acquire the first frame at a first time.

1304 Process the first frame to obtain a first set of attributes of the first frame, including segmenting one or more features from the first frame after one or more first probe-specific effects are reduced in the first frame based at least in part on the first set of control parameters.

> 1306 Reduce the one or more first probe-specific effects in the first frame includes one or more of the group consisting of: preprocessing the first frame to account for the first set of control parameters, and the second set of control parameters, and removing noise from the first frame.
>
>> 1308 Preprocess the first frame to account for the first set of control parameters includes resizing pixels in the first frame, and removing noise from the first frame includes subtracting noise from the first frame using a noise profile specific to the first probe device, and rescale a magnitude of values associated with respective pixels in the first frame.
>>
>>> 1310 Rescale the magnitude of the values associated with the respective pixels to a rescaled range comprises using machine learning to dynamically determine the rescaled range.

1312 Segment the one or more features from the first frame using one or more spatial locations derived from the second frame.

> 1314 Segment the first frame into the one or more features based on the spatial locations derived from the second frame includes obtaining the spatial locations from the template, perform a local search in a window centered at coordinates corresponding to the spatial locations.

1316 The second frame is acquired using a second probe device different from the first probe device.

(A)

Figure 13A 1300 (cont'd) 

1318 In accordance with a determination that the first frame contains a respective attribute present in a second frame acquired at a time earlier than the first time using a second set of control parameters: display, on a user interface, information related to differences in the respective attribute based on the first frame and the second frame, the second frame is obtained by processing the one or more features segmented from the second frame after one or more second probe-specific effects are reduced in the second frame.

| 1320 Display information about changes to the one or more segmented features that are clinically relevant. |

| 1322 Process the one or more features segmented from the second frame includes mapping the one or more features onto a template. |

| 1324 The template includes one or more markers that identify locations of one or more anatomical regions of interest, the one or more anatomical regions of interest include a first anatomical region of interest in which the respective attribute is located. |

Figure 13B

1326 In accordance with a determination that the first frame fails to meet a first criteria related to an anatomical region of interest for positioning the first probe device at a different location from a location where the first frame was acquired to obtain a third frame of a structure within the anatomical region of interest, the third frame having a higher image quality metric compared to the first frame.

1328 Generate a statistical model based on the one or more features to determine a presence of an anatomical region of interest in the first frame.

1330 In accordance with a determination that the first criteria related to the anatomical region of interest have been met, compute a metric of interest associated with the structure.

1332 Process the third frame by segmenting one or more features from the third frame after one or more probe-specific effects are reduced in the third frame, and display, on the user interface, information related to differences in the structure based on the third frame and the second frame.

1334 The third frame is obtained from approximately a same plane and/or in a comparable field of view as the second frame.

1336 The one of more features segmented from the first image comprises features that are invariant to the first probe device.

1338 The first frame is obtained by selecting a frame from a plurality of frames acquired in a sweep.

1340 Obtain a second frame of the probed region acquired using a second probe device, and a second set of control parameters used to acquire the second frame; and process the second frame to obtain a second set of attributes of the second frame, wherein processing the second frame includes segmenting one or more features from the second frame after one or more second probe-specific effects are reduced in the second frame based at least in part on the second set of control parameters.

1402 Display a user interface for presenting an analysis of a second frame of a structure obtained using a second probe device, wherein the second frame of the structure is obtained at a second time after a first frame of the respective attribute is obtained at a first time using a first probe device.

1402 Display, on the user interface, information related to differences in the structure based on the first frame and the second frame, wherein the differences are characterized by processing one or more features segmented from the second frame after one or more probe-specific effects are reduced in the second frame and using one or more spatial locations derived from the first frame.

Figure 14

DEVICE AGNOSTIC SYSTEMS AND METHODS FOR ACQUIRING AND ANALYZING IMAGES FROM AN ULTRASOUND PROBE

TECHNICAL FIELD

The disclosed implementations relate generally to systems, methods, and devices for utilizing an ultrasound probe.

BACKGROUND

Ultrasound imaging is an imaging method that uses sound waves to produce images of structures or features within a region probed by the sound waves. In biological or medical applications, ultrasound images can be captured in real-time to show movement of internal organs as well as blood flowing through the blood vessels. The images can provide valuable information for diagnosing and directing treatment for a variety of diseases and conditions.

SUMMARY

Medical ultrasound is an imaging modality that is based on the reflection of propagating sound waves at the interface between different tissues. Advantages of ultrasound imaging with respect to other imaging modalities may include one or more of: (1) its non-invasive nature, (2) its reduced costs, (3) its portability and (4) its ability to provide a good temporal resolution, for example on the order of millisecond or better. Point-of-care ultrasound (POCUS) may be used at bedside by healthcare providers as a real-time tool for answering clinical questions (e.g., whether a patient has developmental hip dysplasia). A trained clinician may perform both the task of acquiring and the task of interpreting ultrasound images, without the need for a radiologist to analyze ultrasound images acquired by a highly trained technician. Depending on specifics of the ultrasound examination, there may still be highly specialized training to learn different protocols for acquiring medically relevant images that are high quality images.

In some embodiments, after a patient is positioned in an appropriate way, a clinician positions the ultrasound probe on the body of the patient and manually starts looking for an appropriate (e.g., an optimal) image that allows the clinician to make an accurate diagnosis. Acquiring the proper image may be a time consuming activity that is performed by trial-and-error, and it may require extensive knowledge of human anatomy. For the diagnosis of some conditions, the clinician may need to perform manual measurements on the acquired images. Further, fatigue caused by repetitive tasks in radiology may lead to an increase in the number of diagnostic errors and decreased diagnosis accuracy.

Computer aided diagnosis (CAD) systems may help clinicians acquire higher quality images, and automatically analyze and measure relevant characteristics in ultrasound images. The methods, systems, and devices described herein may have one or more advantages, including (1) the ability to incorporate medical-expert domain knowledge in the machine learning algorithms for an efficient learning with a limited number of instances, (2) the ability to interpret outputs of the machine learning algorithms, and (3) the ability to account for discrepancies between probability distributions of images acquired with probes from different manufacturers. A system that lacks the ability to account for discrepancies between probability distributions of images acquired using different probes may not be able to ensure that an automated system that works on images acquired with a first probe (e.g., a probe from a first manufacturer) will also work on images acquired with a second probe (e.g., a probe from a second manufacturer, different from the first manufacturer), hindering the successful development of a product that automatically analyzes ultrasound images and provides guidance to clinicians to help them acquire better ultrasound images in less time.

In some embodiments, the methods, systems and devices described herein provide a device agnostic assessment of ultrasound images, and provide guidance to users to help them acquire images that meet the minimum requirements for making a diagnosis.

In some embodiments, the evolution of an anatomical structure of interest over time is automatically tracked, for example, to monitor the presence or characteristics of tumors in a patient, using follow-up scans, which then form a sequence of ultrasound images acquired at different time-points. In some embodiments, the tracking/follow-up process includes automatically (e.g., without additional input from an operator of the ultrasound system): (1) identifying the same anatomical structure of interest in different images over time, (2) characterizing that anatomical structure of interest by extracting a set of relevant features in each of the different images, and (3) comparing the extracted features over time.

In some embodiments, for comparing the anatomical structure of interest in the new image with the ones acquired in the past, the positioning of the patient and the probe should be as similar as possible to that used for acquiring the original image. Since the information about positioning may not be stored, it may be very challenging to acquire images of the anatomical region of interest that have enough quality to make a meaningful comparison. This problem may become even more challenging when the image is acquired with different probes, since the quality of the images may vary.

There is therefore a need to develop a methodology that allows clinicians to automatically, quickly and reliably, identify and characterize anatomical structures of interest in follow-up scans using ultrasound imaging regardless of the ultrasound device or probe used to acquire such images.

Portable (e.g., handheld, and/or battery-operated) ultrasound devices are capable of producing high quality images because they contain many (e.g., hundreds or thousands) transducers that can each produce sound waves and receive the echoes for creating an ultrasound image. As disclosed herein, the ultrasound probe (or the computing device) guides the operator by providing guidance on how to position the ultrasound probe so as to obtain a high-quality frame that contains the anatomical structures of interest.

The systems, methods, and devices of this disclosure each have several innovative aspects, the desirable attributes disclosed herein may be derived from one or more of the innovative aspects individually or as a combination, in accordance with some embodiments.

In accordance with some embodiments, a method of tracking a structure over time includes at a computer system that includes one or more processors and memory obtaining a first frame of a probed region acquired using a first probe device at a first time, and a first set of control parameters used to acquire the first frame; processing the first frame to obtain a first set of attributes of the first frame, wherein processing the first frame includes segmenting one or more features from the first frame after one or more first probe-specific effects are reduced in the first frame based at least in part on the first set of control parameters. In accordance with a determination that the first frame contains a respective attribute present in a second frame acquired at a time earlier than the first time in using a second set of control parameters, the method includes displaying, on a user interface, information related to differences in the respective attribute based on the first frame and the second frame between the first time and the earlier time. The second frame is obtained by processing the one or more features segmented from the second frame after one or more second probe-specific effects are reduced in the second frame.

In accordance with some embodiments, an ultrasound probe includes a plurality of transducers and a control unit. The control unit is configured to perform any of the methods disclosed herein.

In accordance with some embodiments, a computer system includes one or more processors and memory. The memory stores memory storing instructions that, when executed by the one or more processors, cause the computer system to perform any of the methods disclosed herein.

In accordance with some embodiments of the present disclosure, a non-transitory computer readable storage medium stores computer-executable instructions. The computer-executable instructions, when executed by one or more processors of a computer system, cause the computer system to perform any of the methods disclosed herein.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 13A-13C illustrate a flowchart diagram for a method of tracking a structure over time, in accordance with some embodiments.

FIG. 14 illustrates a flowchart diagram for a method of tracking a structure over time, in accordance with some embodiments.

Reference will now be made to implementations, examples of which are illustrated in the accompanying drawings. In the following description, numerous specific details are set forth in order to provide a thorough understanding of the present invention. However, it will be apparent to one of ordinary skill in the art that the present invention may be practiced without requiring some of these specific details.

DESCRIPTION OF IMPLEMENTATIONS

Figure 1:
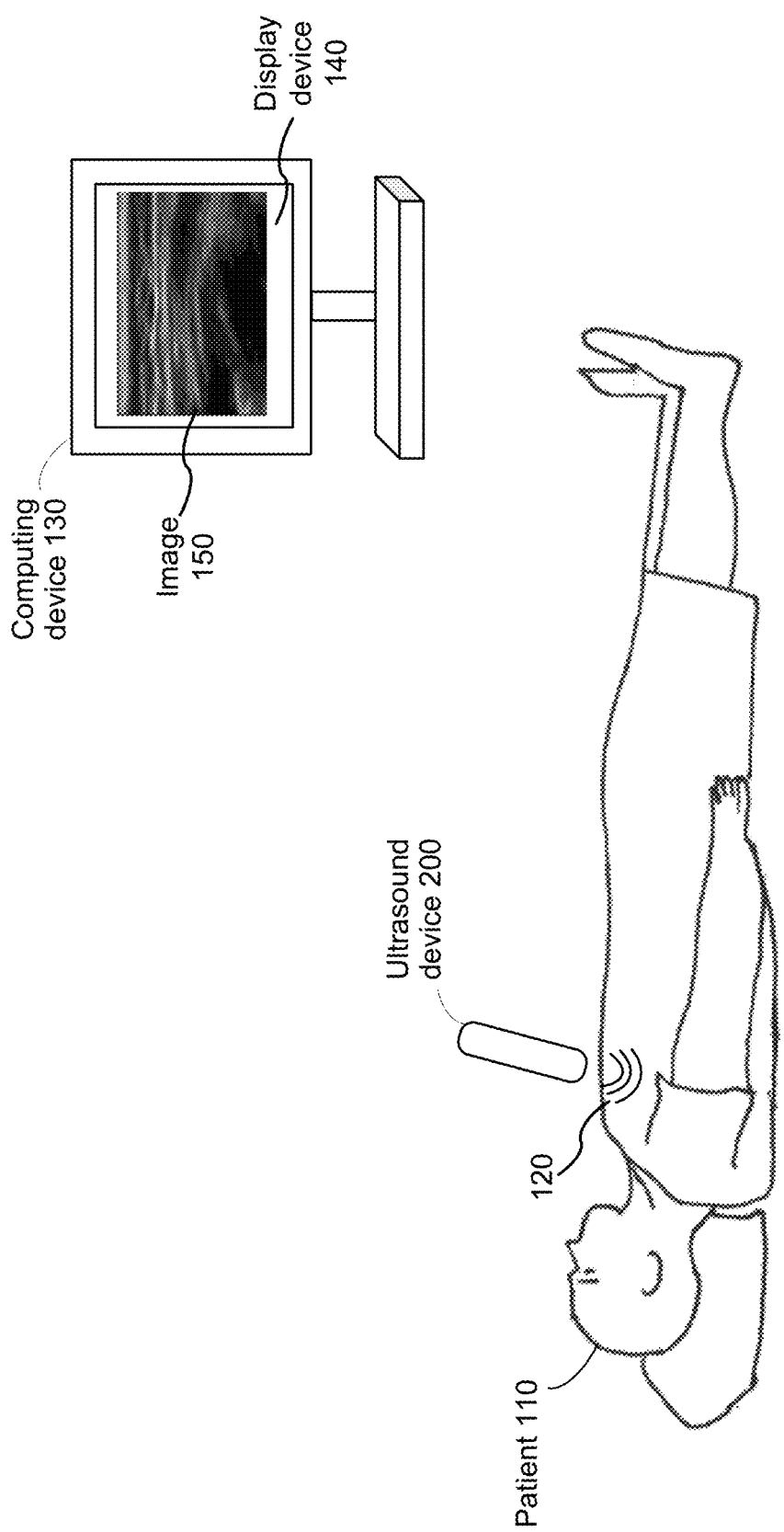
FIG. 1 illustrates an ultrasound system for imaging a patient, in accordance with some embodiments.

FIG. 1 illustrates an ultrasound system for imaging a patient, in accordance with some embodiments.

In some embodiments, the ultrasound device 200 is a portable, handheld device. In some embodiments, the ultrasound device 200 includes a probe portion that includes transducers (e.g., transducers 220, FIG. 2). In some embodiments, the transducers are arranged in an array. In some embodiments, the ultrasound device 200 includes an integrated control unit and user interface. In some embodiments, the ultrasound device 200 includes a probe that communicates with a control unit and user interface that is external to the housing of the probe itself. During operation, the ultrasound device 200 (e.g., via the transducers) produces sound waves that are transmitted toward an organ, such as a heart or a lung, of a patient 110. The internal organ, or other object(s) to be imaged, may reflect a portion of the sound waves 120 toward the probe portion of the ultrasound device 200, which are received by the transducers 220. In some embodiments, the ultrasound device 200 transmits the received signals to a computing device 130, which uses the received signals to create an image 150 that is also known as a sonogram. In some embodiments, the computing device 130 includes a display device 140 for displaying ultrasound images, and other input and output devices (e.g., keyboard, touch screen, joystick, touchpad, and/or speakers).

Figure 2:
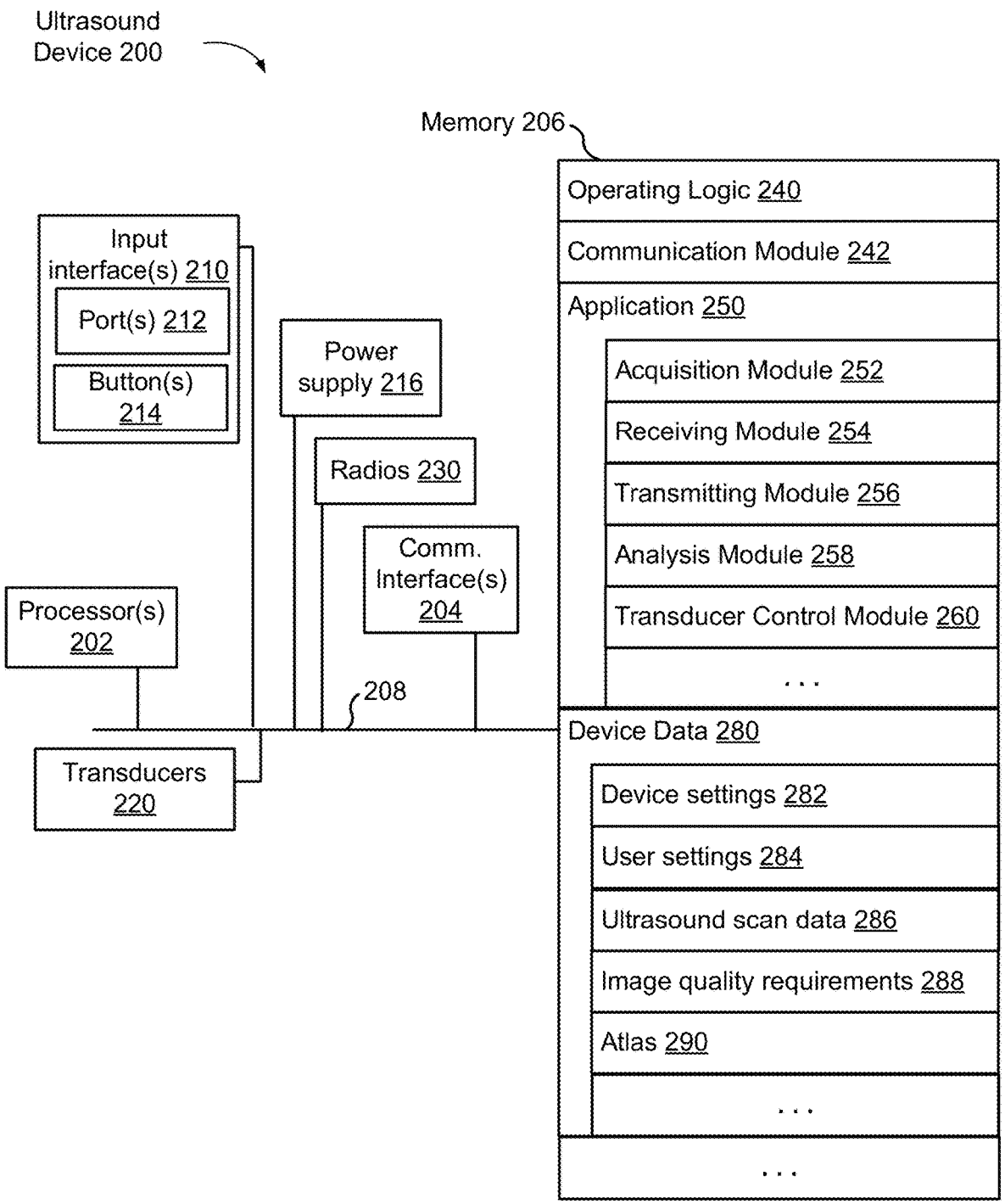
FIG. 2 illustrates a block diagram of an ultrasound device in accordance with some embodiments.

FIG. 2 illustrates a block diagram of an example ultrasound device 200 in accordance with some embodiments.

In some embodiments, the ultrasound device 200 includes one or more processors 202, one or more communication interfaces 204 (e.g., network interface(s)), memory 206, and one or more communication buses 208 for interconnecting these components (sometimes called a chipset).

In some embodiments, the ultrasound device 200 includes one or more input interfaces 210 that facilitate user input. For example, in some embodiments, the input interfaces 210 include port(s) 212 and button(s) 214. In some embodiments, the port(s) can be used for receiving a cable for powering or charging the ultrasound device 200, or for facilitating communication between the ultrasound probe and other devices (e.g., computing device 130, computing device 300, display device 140, printing device, and/or other input output devices and accessories).

In some embodiments, the ultrasound device 200 includes a power supply 216. For example, in some embodiments, the ultrasound device 200 is battery-powered. In some embodiments, the ultrasound device is powered by a continuous AC power supply.

In some embodiments, the ultrasound device 200 includes a probe portion that includes transducers 220, which may also be referred to as transceivers or imagers. In some embodiments, the transducers 220 are based on photoacoustic or ultrasonic effects. For ultrasound imaging, the transducers 220 transmit ultrasonic waves towards a target (e.g., a target organ, blood vessels, etc.) to be imaged. The transducers 220 receive reflected sound waves (e.g., echoes) that bounce off body tissues. The reflected waves are then converted to electrical signals and/or ultrasound images. In some embodiments, the probe portion of the ultrasound device 200 is separately housed from the computing and control portion of the ultrasound device. In some embodiments, the probe portion of the ultrasound device 200 is integrated in the same housing as the computing and control portion of the ultrasound device 200. In some embodiments, part of the computing and control portion of the ultrasound device is integrated in the same housing as the probe portion, and part of the computing and control portion of the ultrasound device is implemented in a separate housing that is coupled communicatively with the part integrated with the probe portion of the ultrasound device. In some embodiments, the probe portion of the ultrasound device has a respective transducer array that is tailored to a respective scanner type (e.g., linear, convex, endocavitary, phased array, transesophageal, 3D, and/or 4D). In the present disclosure, "ultrasound probe" may refer to the probe portion of an ultrasound device, or an ultrasound device that includes a probe portion.

In some embodiments, the ultrasound device 200 includes radios 230. The radios 230 enable one or more communication networks, and allow the ultrasound device 200 to communicate with other devices, such as the computing device 130 in FIG. 1, the display device 140 in FIG. 1, and/or the computing device 300 in FIG. 3. In some implementations, the radios 230 are capable of data communications using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, Ultrawide Band (UWB), software defined radio (SDR) etc.) custom or standard wired protocols (e.g., Ethernet, HomePlug, etc.), and/or any other suitable communication protocol, including communication protocols not yet developed as of the filing date of this document.

The memory 206 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 206, optionally, includes one or more storage devices remotely located from one or more processor(s) 202. The memory 206, or alternatively the non-volatile memory within the memory 206, includes a non-transitory computer-readable storage medium. In some implementations, the memory 206, or the non-transitory computer-readable storage medium of the memory 206, stores the following programs, modules, and data structures, or a subset or superset thereof:

- operating logic 240 including procedures for handling various basic system services and for performing hardware dependent tasks;
- a communication module 242 (e.g., a radio communication module) for connecting to and communicating with other network devices (e.g., a local network, such as a router that provides Internet connectivity, networked storage devices, network routing devices, server systems, computer device 130, computer device 300, and/or other connected devices etc.) coupled to one or more communication networks via the communication interface(s) 204 (e.g., wired or wireless);
- application 250 for acquiring ultrasound data (e.g., imaging data) of a patient, and/or for controlling one or more components of the ultrasound device 200 and/or other connected devices (e.g., in accordance with a determination that the ultrasound data meets, or does not meet, certain conditions). In some embodiments, the application 250 includes:
  - an acquisition module 252 for acquiring ultrasound data. In some embodiments, the ultrasound data includes imaging data. In some embodiments, the acquisition module 252 activates the transducers 220 (e.g., less than all of the transducers 220, different subset(s) of the transducers 220, all the transducers 220, etc.) according to whether the ultrasound data meets one or more conditions associated with one or more quality requirements;
  - a receiving module 254 for receiving ultrasound data;
  - a transmitting module 256 for transmitting ultrasound data to other device(s) (e.g., a server system, computer device 130, computer device 300, display device 140, and/or other connected devices etc.);
  - an analysis module 258 for analyzing whether the data (e.g., imaging data) acquired by the ultrasound device 200 meets one or more conditions associated with quality requirements for an ultrasound scan. For example, in some embodiments, the one or more conditions include one or more of: a condition that the imaging data includes one or more newly acquired images that meet one or more threshold quality scores, a condition that the imaging data includes one or more newly acquired images that correspond to one or more anatomical planes that match a desired anatomical plane of a target anatomical structure, a condition that the imaging data includes one or more newly acquired images that include one or more landmark/features (or a combination of landmarks/features), a condition that the imaging data includes one or more newly acquired images that include a feature having a particular dimension, a condition that the imaging data supports a prediction that an image meeting one or more requirements would be acquired in the next one or more image frames, a condition that the imaging data supports a prediction that a first change (e.g., an increase by a percentage, or number) in the number of transducer used would support an improvement in the quality score of an image acquired in the next one or more image frames, and/or other analogous conditions; and
  - a transducer control module 260 for activating (e.g., adjusting) a number of transducers 220 during portions of an ultrasound scan based on a determination that the ultrasound data meets (or does not meet) one or more quality requirements; and device data 280 for the ultrasound device 200, including but not limited to:

- device settings 282 for the ultrasound device 200, such as default options and preferred user settings. In some embodiments, the device settings 282 include imaging control parameters. For example, in some embodiments, the imaging control parameters include one or more of: a number of transducers that are activated, a power consumption threshold of the probe, an imaging frame rate, a scan speed, a depth of penetration, and other scan parameters that control the power consumption, heat generation rate, and/or processing load of the probe;
- user settings 284, such as a preferred gain, depth, zoom, and/or focus settings;
- ultrasound scan data 286 (e.g., imaging data) that are acquired (e.g., detected, measured) by the ultrasound device 200 (e.g., via transducers 220);
- image quality requirements data 288. In some embodiments, the image quality requirements data 288 include clinical requirements for determining the quality of an ultrasound image; and
- an atlas 290. In some embodiments, the atlas 290 includes anatomical structures of interest. In some embodiments, the atlas 290 includes three-dimensional representations of the anatomical structure of interest (e.g., hip, heart, lung, and/or other anatomical structures).

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 206 stores a subset of the modules and data structures identified above. Furthermore, the memory 206 may store additional modules or data structures not described above. In some embodiments, a subset of the programs, modules, and/or data stored in the memory 206 are stored on and/or executed by a server system, and/or by an external device (e.g., computing device 130 or computing device 300).

Figure 3:
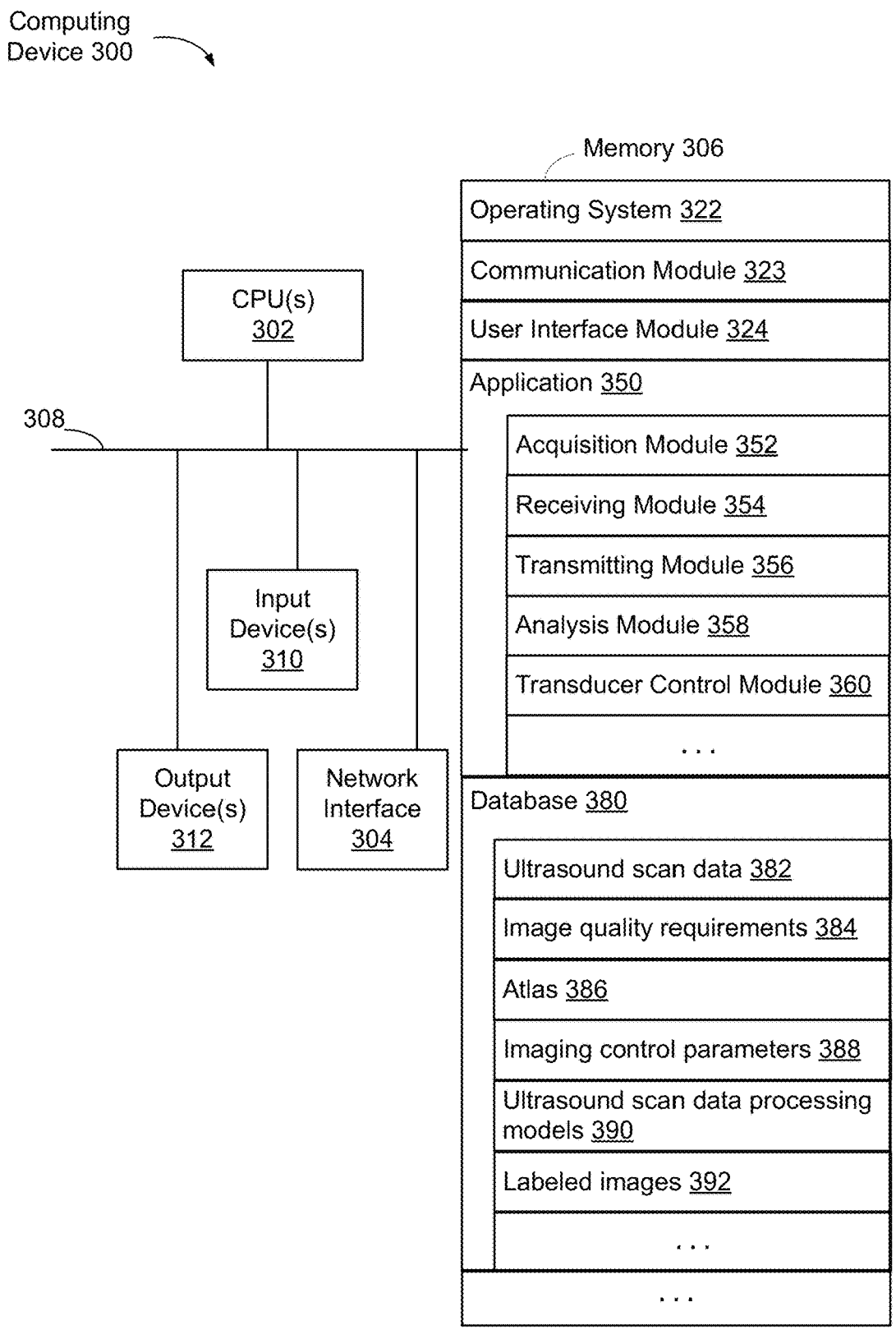
FIG. 3 illustrates a block diagram of a computing device in accordance with some embodiments.

FIG. 3 illustrates a block diagram of a computing device 300 in accordance with some embodiments.

In some embodiments, the computing device 300 is a server or control console that is in communication with the ultrasound device 200. In some embodiments, the computing device 300 is integrated into the same housing as the ultrasound device 200. In some embodiments, the computing device is a smartphone, tablet device, a gaming console, or other portable computing devices.

The computing device 300 includes one or more processors 302 (e.g., processing units of CPU(s)), one or more network interfaces 304, memory 306, and one or more communication buses 308 for interconnecting these components (sometimes called a chipset), in accordance with some implementations.

In some embodiments, the computing device 300 includes one or more input devices 310 that facilitate user input, such as a keyboard, a mouse, a voice-command input unit or microphone, a touch screen display, a touch-sensitive input pad, a gesture capturing camera, or other input buttons or controls. In some embodiments, the computing device 300 uses a microphone and voice recognition or a camera and gesture recognition to supplement or replace the keyboard. In some embodiments, the computing device 300 includes one or more output devices 312 that enable presentation of user interfaces and display content, such as one or more speakers and/or one or more visual displays (e.g., display device 140).

The memory 306 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 306, optionally, includes one or more storage devices remotely located from the one or more processors 302. The memory 306, or alternatively the non-volatile memory within the memory 306, includes a non-transitory computer-readable storage medium. In some implementations, the memory 306, or the non-transitory computer-readable storage medium of the memory 306, stores the following programs, modules, and data structures, or a subset or superset thereof:

- an operating system 322 including procedures for handling various basic system services and for performing hardware dependent tasks;
- a communication module 323 (e.g., a radio communication module) for connecting to and communicating with other network devices (e.g., a local network, such as a router that provides Internet connectivity, networked storage devices, network routing devices, server systems, computer device 130, ultrasound device 200, and/or other connected devices etc.) coupled to one or more communication networks via the network interface 304 (e.g., wired or wireless);
- a user interface module 324 for enabling presentation of information (e.g., a graphical user interface for presenting application(s), widgets, websites and web pages thereof, games, audio and/or video content, text, etc.) either at the computing device 300 or another device;
- application 350 for acquiring ultrasound data (e.g., imaging data) from a patient. In some embodiments, the application 350 is used for receiving data (e.g., ultrasound data, imaging data, etc.) acquired via an ultrasound device 200. In some embodiments, the application 350 is used for controlling one or more components of an ultrasound device 200 (e.g., the probe portion, and/or the transducers) and/or other connected devices (e.g., in accordance with a determination that the data meets, or does not meet, certain conditions). In some embodiments, the application 350 includes:
  - an acquisition module 352 for acquiring ultrasound data. In some embodiments, the ultrasound data includes imaging data acquired by an ultrasound probe. In some embodiments, the acquisition module 352 activates the transducers 220 (e.g., less than all of the transducers 220, different subset(s) of the transducers 220, all the transducers 220, etc.) according to whether the ultrasound data meets one or more conditions associated with one or more quality requirements. In some embodiments, the acquisition module 352 causes the ultrasound device 200 to activate the transducers 220 (e.g., less than all of the transducers 220, different subset(s) of the transducers 220, all the transducers 220, etc.) according to whether the ultrasound data meets one or more conditions associated with one or more quality requirements;

a receiving module 354 for receiving ultrasound data. In some embodiments, the ultrasound data includes imaging data acquired by an ultrasound probe;

a transmitting module 356 for transmitting ultrasound data (e.g., imaging data) to other device(s) (e.g., a server system, computer device 130, display device 140, ultrasound device 200, and/or other connected devices etc.);

an analysis module 358 for analyzing whether the data (e.g., imaging data, power consumption data, and other data related to the acquisition process) (e.g., received by the ultrasound probe) meets one or more conditions associated with quality requirements for an ultrasound scan. For example, in some embodiments, the one or more conditions include one or more of: a condition that the imaging data includes one or more newly acquired images that meet one or more threshold quality scores, a condition that the imaging data includes one or more newly acquired images that correspond to one or more anatomical planes that match a desired anatomical plane of a target anatomical structure, a condition that the imaging data includes one or more newly acquired images that include one or more landmark/features (or a combination of landmarks/features), a condition that the imaging data includes one or more newly acquired images that include a feature having a particular dimension, a condition that the imaging data supports a prediction that an image meeting one or more requirements would be acquired in the next one or more image frames, a condition that the imaging data supports a prediction that a first change (e.g., an increase by a percentage, or number) in the number of transducer used would support an improvement in the quality score of an image acquired in the next one or more image frames, and/or other analogous conditions; and a transducer control module 360 for activating (e.g., adjusting, controlling, and/or otherwise modifying one or more operations of the transducers), or causing the ultrasound device 200 to activate (e.g., via the transducer control module 260), a number of transducers 220 during portions of an ultrasound scan based on a determination that the ultrasound data meets (or does not meet) one or more quality requirements. For example, in some embodiments, the transducer control module 360 activates a first subset of the transducers 220 during the first portion of an ultrasound scan. In some embodiments, the transducer control module 360 activates a second subset of the transducers 220, different from the first subset of the transducers, during a second portion of the scan following the first portion of the scan, when the imaging data corresponding to the first portion of the scan meets (or does not meet) one or more quality requirements. In some embodiments, the transducer control module 360 controls one or more operating modes of the ultrasound device 200. For example, in some embodiments, the ultrasound device 200 is configured to operate in a low-power mode. In the low-power mode, the transducer control module 360 activates only a subset (e.g., 10%, 15%, 20%, etc.) of all the available transducers 220 in the ultrasound device 200. In some embodiments, the ultrasound device 200 is configured to operate in a full-power mode. In the full-power mode, the transducer control module 360 activates all the available transducers 220 to acquire a high-quality image; and a database 380, including:
ultrasound scan data 382 (e.g., imaging data) that are acquired (e.g., detected, measured) by one or more ultrasound devices 200;
image quality requirements data 384. In some embodiments, the image quality requirements data 384 include clinical requirements for determining the quality of an ultrasound image;
an atlas 386. In some embodiments, the atlas 386 includes anatomical structures of interest. In some embodiments, the atlas 386 includes three-dimensional representations of the anatomical structure of interest (e.g., hip, heart, or lung);
imaging control parameters 388. For example, in some embodiments, the imaging control parameters include one or more of: a number of transducers that are activated, a power consumption threshold of the probe, an imaging frame rate, a scan speed, a depth of penetration, and other scan parameters that control the power consumption, heat generation rate, and/or processing load of the probe;
ultrasound scan data processing models 390 for processing ultrasound data. For example, in some embodiments, the ultrasound scan data processing models 390 are trained neural network models that are trained to determine whether an ultrasound image meets quality requirements corresponding to a scan type, or trained to output an anatomical plane corresponding to an anatomical structure of an ultrasound image, or trained to predict, based on a sequence of ultrasound images and their quality scores, whether a subsequent frame to be acquired by an ultrasound probe will contain certain anatomical structures and/or landmarks of interest; and
labeled images 392 (e.g., a databank of images), including images for training the models that are used for processing new ultrasound data, and/or new images that have been or need to be processed. In some embodiments, the labeled images 392 are images of anatomical structures that have been labeled with their respective identifiers and relative positions.

Each of the above identified elements may be stored in one or more of the memory devices described herein, and corresponds to a set of instructions for performing the functions described above. The above identified modules or programs need not be implemented as separate software programs, procedures, modules or data structures, and thus various subsets of these modules may be combined or otherwise re-arranged in various embodiments. In some embodiments, the memory 306, optionally, stores a subset of the modules and data structures identified above. Furthermore, the memory 306 optionally stores additional modules and data structures not described above. In some embodiments, a subset of the programs, modules, and/or data stored in the memory 306 are stored on and/or executed by the ultrasound device 200.

Figure 4:
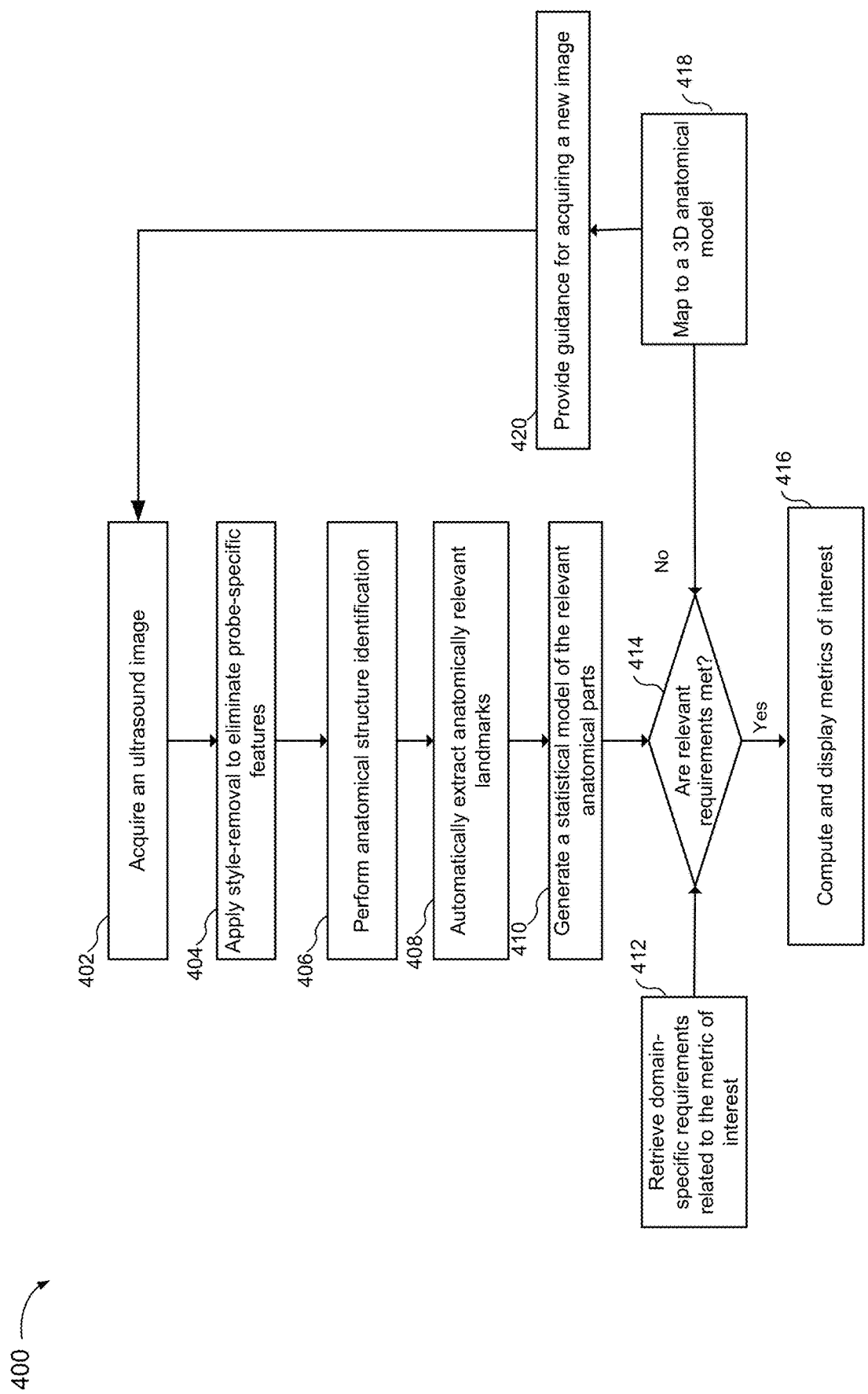
FIG. 4 is a workflow in a device-agnostic guidance system for acquiring ultrasound images, in accordance with some embodiments.

FIG. 4 is a workflow in a device-agnostic guidance system for acquiring ultrasound images, in accordance with some embodiments. In some embodiments, the ultrasound images are medical ultrasound images used for diagnostic purposes. In some embodiments, the workflow 400 is performed by one or more processors (e.g., CPU(s) 302) of a computing device that is communicatively connected with an ultrasound probe. For example, in some embodiments, the computing device is a server or control console (e.g., a server, a standalone computer, a workstation, a smart phone, a tablet device, a medical system) that is in communication with the ultrasound probe. In some embodiments, the computing device is a control unit integrated into the ultrasound probe. In some embodiments, the ultrasound probe is a handheld ultrasound probe or an ultrasound scanning system.

Figure 5A:
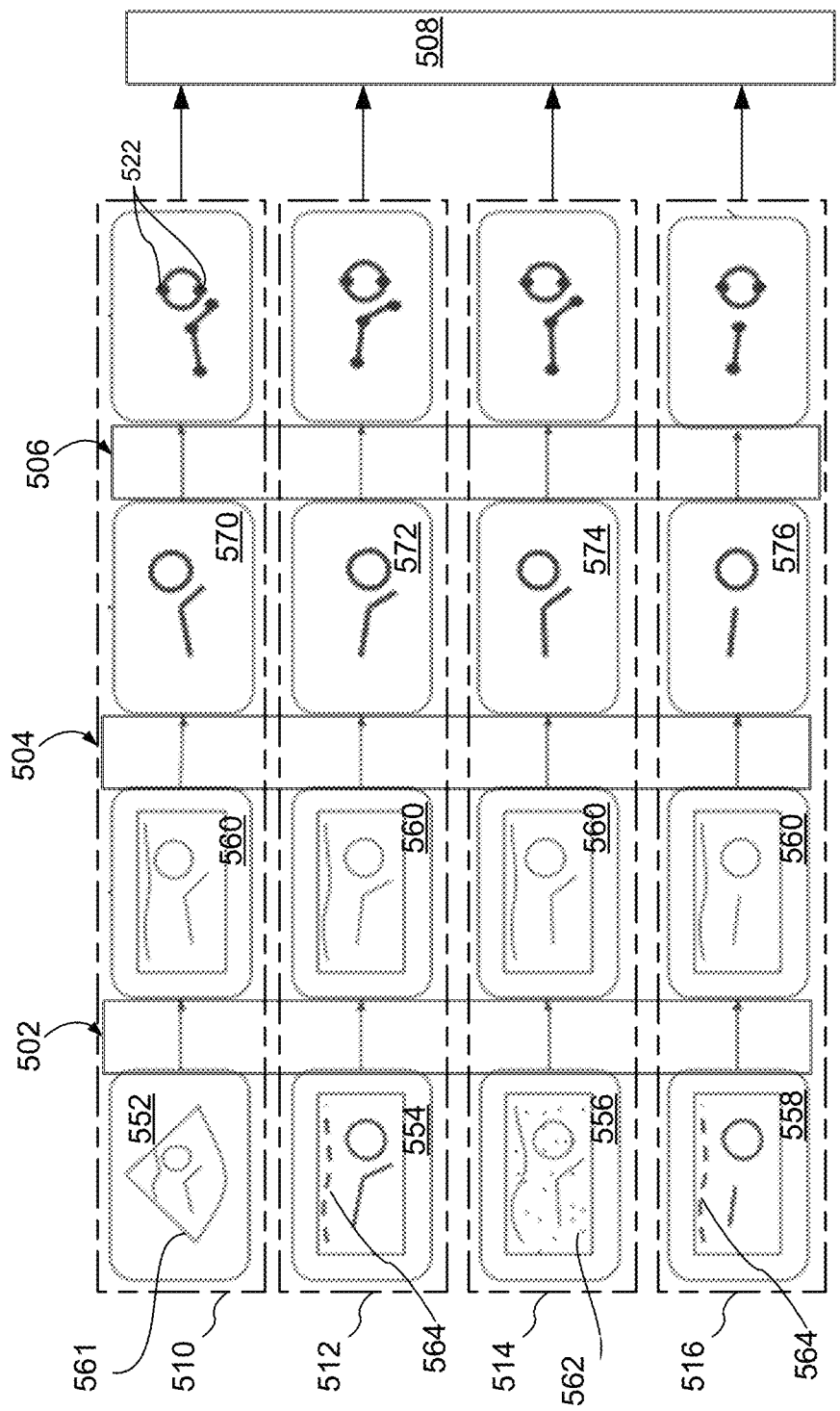
FIGS. 5A and 5B provide an example of acquiring medical ultrasound images for diagnosing hip dysplasia, in accordance with some embodiments.

In some embodiments, the workflow 400 includes acquiring (402) medical images, such as ultrasound images, In some embodiments, the ultrasound image is an ultrasound image frame that meets one or more quality requirements for making a diagnosis and/or other conditions. Ultrasound examinations are typically done by placing (e.g., pressing) a portion of an ultrasound device (e.g., an ultrasound probe or scanner) against a surface or inside a cavity of a patient's body, adjacent to the area being studied. An operator (e.g., a clinician) moves the ultrasound device around an area of a patient's body until the operator finds a location and pose of the probe that results in an image of the anatomical structures of interest with sufficiently high quality. The workflow 400 is further illustrated by an example of acquiring medical ultrasound images for diagnosing hip dysplasia, in accordance with some embodiments, in FIGS. 5A and 5B. The ultrasound probe may acquire the images using one or more of its acquisition modalities, including a single (e.g., static) 2D image, an automated sweep yielding a series of (static) images for different 2D planes (referred to herein as a "2D sweep"), a cine clip, which is a real time video capture of scanned anatomy, or a single scan that acquires a 3D volume of images corresponding to a number of different 2D planes (referred to herein as a "3D scan"). Original images 552, 554, 556, and 558 acquired using one or more ultrasound devices in the step 402 are processed in respective sequences 510, 512, 514, and 516, as shown in FIG. 5A.

In some embodiments, the workflow 400 includes applying (404) a style-removal process to reduce (e.g., eliminate) probe-specific features. As used herein, the term probe-specific effects refers to effects within resulting images that differ from probe-to-probe. Some probe-specific effects are based on the model or manufacturer of the probe, whereas other probe-specific effects may result from differences between two instances of the same model. Probe-specific features (e.g., caused by probe-specific effects) may degrade the performance of artificial intelligence (AI) systems used to analyze those images. For example, a classifier trained using images acquired with a first probe (e.g., a probe from a first manufacturer) may achieve a performance of 95%. But when the same classifier is used on images acquired with a second probe (e.g., a probe from a second manufacturer, different from the first manufacturer), the classifier may have a performance of 70%. Device-agnostic algorithms (e.g., that include style-removal steps) may provide a predictor (e.g., a classifier, or other machine learning models) whose performance does not degrade (or whose performance degradation is reduced) when provided with images acquired using different probes. FIG. 5A illustrates different aspects of the style removal process.

Style Removal Process

A style-removal process 502 (e.g., using a style-removal algorithm) is applied to the original images (e.g., original images 552, 554, 556, and 558) acquired during the step 402 (e.g., the image acquisition step). The style-removal process 502 maps the original images into a common space 560. In some embodiments, the common space 560 is common to ultrasound images (e.g., all ultrasound images) of the same anatomical region in a particular view, even for ultrasound images acquired by probes having different characteristics (e.g., power, zoom-factor, depth, frequency, or a size of a field of view). The style-removal process 502 helps minimize the probability that a guidance system works well only for images acquired with a first probe but not images acquired with a different probe. In some embodiments, the style-removal process 502 removes features from the images that are attributable to specific probes (e.g., noise artifacts specific to a particular probe) leaving behind features in the images that are related to the anatomical region that is interrogated by the probe but are not specific to any particular probe.

In some embodiments, the style-removal algorithm includes a machine learning algorithm that minimizes (e.g., explicitly minimizes) the divergence between batches of images (or a vector representation of those images) acquired with different probes. For example, as shown in FIG. 5A, the original image 552 has a sector shaped field of view 561, while the other three original images 554, 556, and 558 have rectangular-shaped fields of view. By minimizing the divergence between the batch of four images to remove style information (e.g., geometric shape of the field of view), the original image 552 is transformed (e.g., via data transformation such as by a geometric projection) to map onto a common space 560 that has a field of view (e.g., a rectangular field of view) that matches the other images.

Similarly, the image 556 may be acquired using a second probe, different from a first probe that was used to acquire one or more of original images 552, 554, and 558. The image 556 includes noise (e.g., a speckle pattern of random noise, or other random noise) that may be specific to the second probe, or is otherwise not present in one or more of the original images 552, 554, and 558. After the style-removal process 502 in the step 404 for the processing sequence 514, the noise 562 is removed from the original image 556 to minimize the divergence between the batch of four original images. Thus, the image 556 is mapped into the common space 560, without the noise 562 that was originally present in the image 556. In some embodiments, the common space is where discrepancies in the pixel distributions (e.g., due to the use of different ultrasound probes) are minimized.

In some embodiments, the original images may include variations or artifacts associated with anatomical features captured in the image. For example, the original images 554 and 558 may have imaging artifacts 564 associated with an anatomical feature. Style removal reduces (e.g., eliminates) variations such as imaging artifacts 564 produced by the ultrasound probe.

Some examples of divergence measures are KL-divergence, Wasserstein distance, maximum mean discrepancy. In some embodiments, the style-removal step includes the use of an algorithm that indirectly minimizes the divergence between the probability distributions of different probes. For example, by applying computer vision, signal processing, image processing, or other feature extraction techniques, noises introduced by the different probes are removed.

Invariant Features

In some embodiments, an invariant feature is a feature that is related to the object being imaged, and not to the image itself. For example, an organ (e.g., a liver) may be scanned with two different probes, each having different noise levels, zoom, and other operational parameters. Invariant features may include one or more of: the real size of the organ, a volume of the organ, a percentage of fat in the organ, a shape of the organ, geometric contours of the organ. Depending on operational parameters of the ultrasound probe (e.g., a zoom factor), the scanned organ may appear bigger or smaller in an acquired ultrasound image. As a result, if a two-dimensional area of the scanned organ is determined by summing up a number of pixels lying within a boundary of the liver, different numbers of pixels will be obtained from different ultrasound images, depending on the operational parameters (e.g., for a zoomed-in image, the number of pixels will be higher than for a zoomed-out image). Thus, the number of pixels is not an invariant feature.

A pixel spacing corresponds to a physical dimension associated with a pixel. The number of pixels divided by the pixel spacing is an invariant feature. For a zoomed-in image, the pixel spacing may be 10 µm, while the pixel spacing may be 1 mm in a zoomed-out image.

In some embodiments, segmenting an anatomical structure of interest (e.g., an organ, such as the liver) may be based at least in part on locating "bright" pixels (e.g., having a pixel intensity greater than a predefined threshold) in an acquired image. However, a predefined threshold may be different for images acquired with different operational settings (e.g., some will be brighter than others, different operational settings may include operations at different frequencies or amplitudes).

An invariant feature that can be extracted from the image may include intensity gradients (e.g., determining gradients and/or local minima in the image by taking a first derivative of adjacent or other neighboring pixel intensities) of the image after the image has been appropriately processed (e.g., undergone the style removal process). In some embodiments, the image is processed using histogram equalization prior to any determination of intensity gradients. Histogram equalization is a method in image processing of contrast adjustment using the image's histogram. In some embodiments, intensity gradients are invariant to linear transformations of pixel intensities.

In addition to extracting information based on intensity gradients of the original images, other image parameters, such as an intensity range recorded in each pixel of the original image may also be changed during the style-removal process. For example, original pixel values in the original image may range from 0-255. By rescaling the values to a smaller range, e.g., between 0-20, noise in the original image can be reduced (e.g., eliminated). An example where such an intensity range rescaling may be useful is for detecting of B-lines in lung scans. In some embodiments, the rescaled pixel value range may be automatically determined (e.g., to ranges other than 0-20) using machine learning methods to maximize performance (e.g., performance of the predictor). In some embodiments, the predictor is more robust when trained with pre-processed (e.g., post-style-removal) images that have a narrower range of pixel intensity values.

Common Space

In some embodiments, a common space may also be called a latent space. In some embodiments, the latent space is a common, shared space and not an observed one. For example, consider a classifier that predicts a health condition (sick vs. healthy) based on heights of people. The height data in the observed space (e.g., physical heights) may not be compared directly, when, for example, heights are measured in different units (e.g., feet and cm, and 6 ft is different from 6 cm). An example of a latent space is a space in which variables are standardized. For example, for each observed value of the variable (e.g., height) from each of the two datasets (e.g., one dataset corresponds to measurements recorded in feet, and the other dataset corresponds to measurements recorded in cm, respectively), the statistical mean (e.g., of the collection of heights measured in the same unit) is subtracted, and the result is divided by the standard deviation (of the collection of heights measured in the same unit). Thus, both datasets (e.g., containing measurements in feet, and cm, respectively) can be independently processed, and the output data can be combined, and analyzed together in the latent space. The standardization process described above produces standard scores that represent the number of standard deviations above or below the mean that a specific observation (e.g., of height) falls. For instance, a standardized value of 2 indicates that the observation falls 2 standard deviations above the mean. This allows height data to be compared regardless of the units in which the original data was collected. In some embodiments, the latent space is not observed but can be computed (e.g., by converting measurement units).

In some embodiments, the differences between original ultrasound images acquired using different probes do not arise from the use of different units, but from differing intensity patterns, noise, and quality associated with each original image. And the style removal process 502 removes those variations in intensity patterns, transforming the images such that the processed images are in the same latent space.

Returning to FIG. 4, the workflow 400 includes identifying (406) anatomical structures from the images in which style-removal has been applied. FIG. 5A illustrates different aspects of the feature identification and segmentation.

Feature Identification and Segmentation

A feature identification and segmentation process 504 is applied to the pre-processed images which have undergone style removal processes during the step 404. The feature identification and segmentation process (e.g., an anatomical structure identification process) 504 identifies relevant anatomical structures present in the common space 560. In some embodiments, a convolutional neural network for segmentation is used to identify the anatomical regions of interest from the acquired image. In some embodiments, template matching approaches are used to identify anatomical regions of interest from the acquired image. In some embodiments, manually defined or selected features (e.g., based on the shape and texture of the anatomical parts to be identified) are defined for identifying anatomical regions of interest from the acquired image.

As a first nonlimiting example, for diagnosis of developmental dysplasia of the hip, structures of interest to be identified from the segmentation process 504 include the iliac bone, the acetabulum, and the femoral head. For the diagnosis of fatty liver, the organs of interest include the liver itself, and the kidney. In FIG. 5A, for example, segmentation masks 570, 572, 574, and 576 all show a circular femoral head. In each of segmentation masks 570, 572 and 574, two linear structures corresponding to the ilium and acetabulum make an obtuse angle with each other, while oriented slightly differently and showing different lengths of the ilium and acetabulum. The segmentation mask 576 shows only a single linear structure slightly angled from a horizontal position.

The workflow 400 includes automatically extracting (408) anatomically relevant landmarks without user intervention using the segmentation masks obtained from the segmentation process 504 as an input.

Landmark Identification

Figure 6:
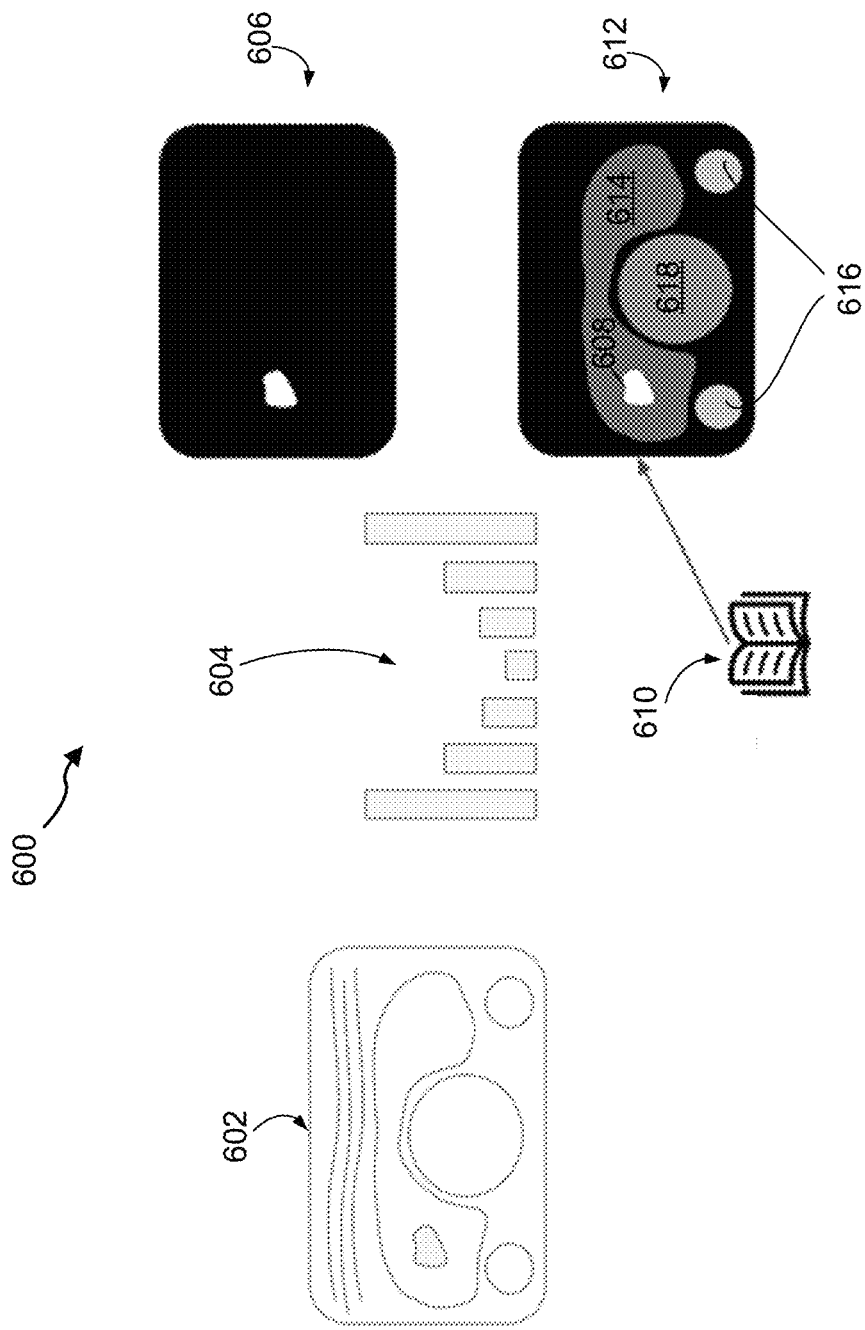
FIG. 6 illustrates an example of a multitask approach for encoding domain specific knowledge into a machine learning algorithm, in accordance with some embodiments.

The output of the segmentation/identification process 504 is provided to a landmark identification process 506 for identifying anatomical landmarks of interest. FIG. 5A and FIG. 6 illustrate different aspects of landmark identification.

Figure 5B:
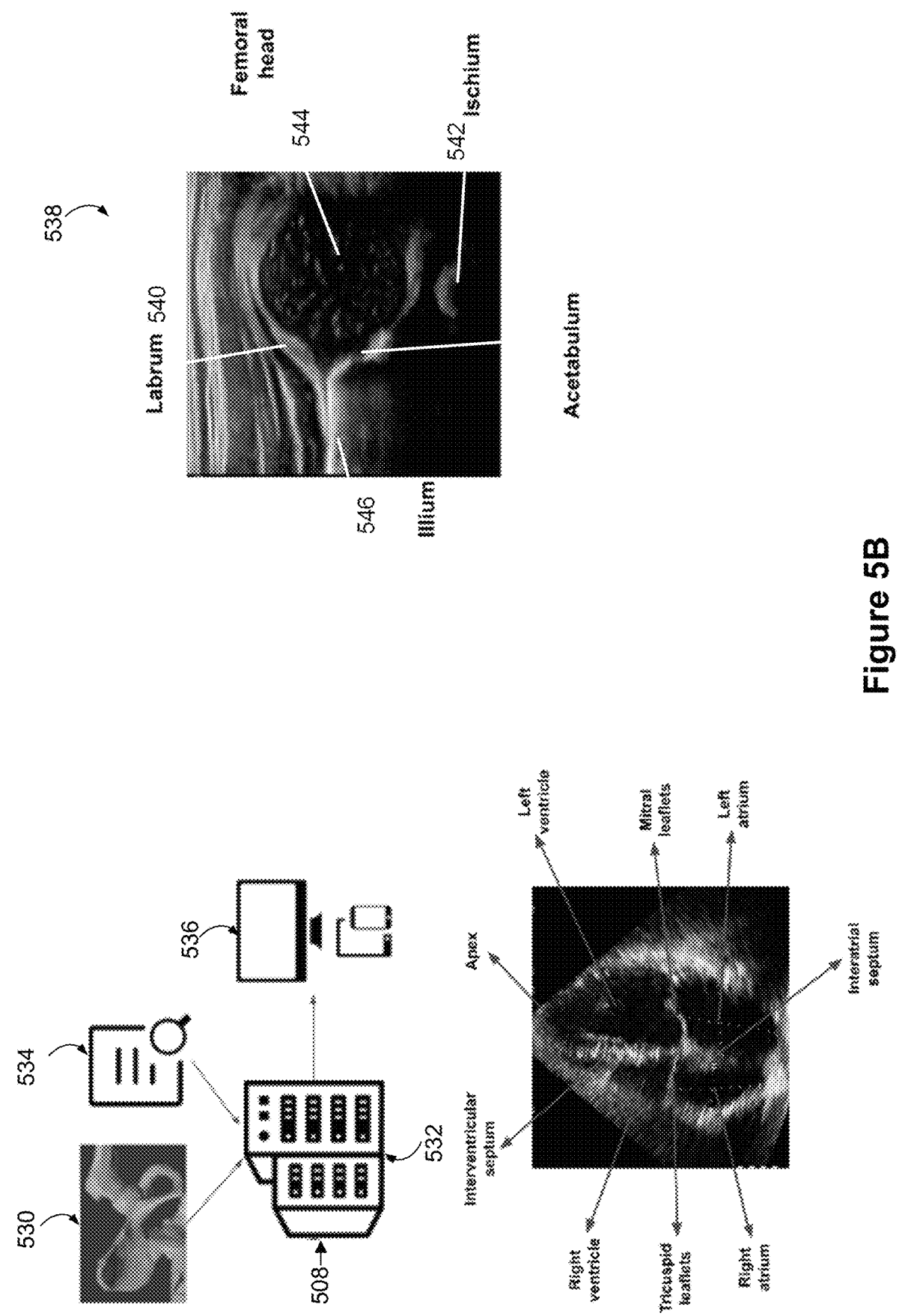

In some embodiments, the landmarks are obtained by a geometrical analysis of the segmentation masks obtained from the segmentation/identification process 504. For example, in embodiments where the diagnostic target is hip dysplasia, the segmentation mask may be circular (e.g., the femoral head), while the masks for identifying B-lines in lung images may be substantially linear. For example, when the segmentation/identification process 504 provides a circular segmentation mask as an output, the landmark identification process 506 may generate landmarks 522 around a circumference of the circular segmentation mark. In some embodiments, landmarks may be obtained by machine learning and image processing methods. As shown in FIG. 5B, an output 508 of the identification process 506 is provided to a computer system 532. The computer system 532 also receives minimum requirements 534 for making clinical diagnosis based on the ultrasound images and data from a 3D model 530. The output of the computer system 532 is provided to a user via a display 536. In some embodiments, an output from the computer system 532 includes presenting metrics of interest for the clinician, in accordance with a determination that all the elements for making the diagnosis are present in the image. In some embodiments, in accordance with a determination that the image does not contain all the elements for making a diagnosis, the computer system 532 then proceeds to an analysis using a convolution neural network (CNN) described below.

In some embodiments, the ultrasound image that is acquired in step 402 is provided as an input to a convolutional neural network (CNN) that is trained to output integer grades (e.g., from 1 to 5) that indicates a range of a proportion of the requirements that the image meets (optionally, more important requirements contribute more to the grade, if met). In some embodiments, the computer system 532 provides guidance on how to position the probe to acquire a better image that contains all the necessary elements for computing the metrics.

The workflow 400 includes generating (410) a statistical model of the relevant anatomical parts. In some embodiments, the statistical model is generated based on landmarks identified from the landmark identification process 506. For example, landmarks are used as priors in a statistical shape model (SSM) to refine the boundaries of the anatomical regions of interest. A statistical shape model is a geometric model that describes a collection of semantically similar objects and represents an average shape of many three-dimensional objects as well as their variation in shape. In some embodiments, semantically similar objects are objects that have visual (e.g., color, shape, or texture) features that are similar and also similarities in "higher level" information, such as possible relations between the objects. In some embodiments, each shape in a training set of the statistical shape model may be represented by a set of landmark points that is consistent from one shape to the next (e.g., for a statistical shape model involving a hand, the fifth landmark point may always correspond to the tip of the thumb).

For example, an initial circular segmentation mask for the femoral head in diagnosing hip dysplasia may have a diameter of a unit length. Based on the output of the landmark identification process 506, the circular segmentation mask may be resized to track positions of the landmarks and have a refined circumferential boundary that is larger than a unit length. The refined segmentation masks (or other outputs) may be used to generate a statistical model of the relevant anatomical parts that provides optimized boundaries for organs and/or anatomical structures present in an image. In some embodiments, the landmarks are provided to the statistical shape model generated in the step 410 to determine if the image collected at the step 402 contains sufficient anatomical information to provide a meaningful clinical decision.

Once the boundaries of the organs or anatomical structures are optimized, the workflow 400 retrieves (412) domain-specific requirements related to a metric of interest and determines (414) whether the image obtained at the step 402 meets the relevant requirements, using the statistical model generated in the step 410. For hip dysplasia, the domain-specific requirements for the metric of interest may include an angle between the acetabulum and ilium, as well as a coverage of the femoral head with respect to the ilium. For example, a lower coverage of the femoral head with respect to the ilium corresponds to a more visible femoral head, increasing its metric of diagnostic relevance. Similarly, an angle between the acetabulum and ilium provides an indication of a plane the image is acquired at, and whether the acquired image meets relevant requirements for rendering a diagnosis. The relevance of various image features is provided as domain-specific requirements relating to the metric of interest.

Training CNN

In some embodiments, the ultrasound image that is acquired in step 402 is used as an input to a trained neural network, such as a convolutional neural network (CNN), which has been trained to determine whether the image complies with all the clinical requirements. The output of this network may be one of n classes. When n is 2, the trained neural network may provide a binary output such as "compliant" or "non-compliant." A compliant image is one that meets the image quality requirements, whereas a non-compliant image is one that does not meet at least one clinical requirement. In some embodiments, the image that is acquired in step 402 is used as an input to a convolutional neural network (CNN) that is trained to output a real number (e.g., from 0 to 1, 0 to 100%, etc.) that indicates a proportion (e.g., a percentage) of or extent to which the requirements that the image meets. In some embodiments, the neural network is configured (e.g., trained) to provide an indication as to which individual requirements are met and which ones are not.

In some embodiments, the neural network is trained by a training data set that includes a set of p images that have been determined as compliant, e.g., by a human expert, and a set of q images that have been labeled as non-compliant, e.g., by a human expert. Each image is input to the convolutional neural network, which includes a set of convolutional layers that is optionally followed by pooling, batch-normalization, dropout, dense, or activation layers. The output of the selected architecture is a vector of length n, where n is the number of classes to be identified. Each entry in the output vector is interpreted as the computed probability of belonging to each of the n classes. The output vector is then compared with a ground truth vector, which contains the actual probability of belonging to each of the n classes. The distance between the output vector and the ground truth vector is then computed using a loss function. Common loss functions are cross-entropy and its regularized versions; however, there are many loss functions that can be used for this process. The loss function is then used to compute an update to the weights. Common optimization methods to compute this update are gradient-based optimization methods, such as gradient descent and its variants. A neural network may be configured to output a real number representing a percentage of requirements that are being currently met by the acquired image. The process of computing the loss and updating the weights is performed iteratively until a predetermined number of iterations is completed, or until a convergence criterion is met. One possible implementation of this approach is to create a set of binary classifiers like the one described above. One binary classifier is trained for each clinical requirement, and the percentage of classifiers with a positive output is then computed.

In accordance with a determination that the image obtained in the step 402 meets the relevant requirements, the workflow 400 computes (416) and displays the metric of interest (e.g., clinical metrics of interest) associated with the image obtained at the step 402.

Quality Metric

The methods and systems described herein also automatically compute metrics that are relevant for assessing if the current ultrasound image meets minimum quality requirements. For example, in the case of hip dysplasia, such requirements are a fully visible femoral head, and an image where the ilium appears as a horizontal line. FIG. 5B shows an example ultrasound image 538 of a hip that meets the clinical requirements for determining the presence of hip dysplasia. As a nonlimiting example, the clinical requirements for an ultrasound image of a hip to determine the presence of hip dysplasia include the presence of labrum 540, ischium 542, the midportion of the femoral head, 544, flat and horizontal ilium 546, and absence of motion artifact.

As another example, the clinical requirements for an echocardiography 4-chamber apical view (as shown in FIG. 5B) are: (i) a view of the four chambers (left ventricle, right ventricle, left atrium, and right atrium) of the heart, (ii) the apex of the left ventricle is at the top and center of the sector, while the right ventricle is triangular in shape and smaller in area, (iii) myocardium and mitral leaflets should be visible, and (iv) the walls and septa of each chamber should be visible.

In accordance with a determination that the image obtained in the step 402 does not meet the relevant requirements, the workflow 400 maps (418) the one or more anatomically relevant structures to a 3D anatomical model. In some embodiments, the workflow 400 maps the one or more anatomically relevant structures to a 3D anatomical model regardless of whether relevant requirements are met. In some embodiments, the 3D anatomical model includes a 3-D dimensional template. Mapping the anatomically relevant structure to the 3D anatomical model can be used to estimate a plane currently being displayed by the image collected at the step 402 (e.g., an image plane associated with the image collected at the step 402). In some embodiments, mapping of the anatomically relevant structure to the 3D anatomical model includes combining medical expertise with segmentation networks (e.g., from the step 406 and/or the process 504) to map the image obtained at the step 402 into a template. The relative location of the image with respect to the template allows the workflow 400 to guide (420) the user on collecting a new image of higher quality that meets the clinical requirements for diagnosis. In some embodiments, the feedback is provided to the user either on a display of the computer system or it may be displayed on a local device (e.g., cell phone or tablet) of the clinician or patient collecting the image. The workflow 400 also includes informing the user how and why one or more requirements are not being met by the image collected at the step 402 (e.g., why the image does not have the desired quality). In some embodiments, the workflow 400 includes receiving or generating a compiled set of characteristics associated with a good quality image and the workflow 400 further displays the information to the user. Unlike other methods that use a black-box approach (e.g., other deep learning models) that receives an image as in input, and outputs a decision or suggested action without providing any justification (e.g., an output message such as "This image is of poor quality with a probability of 55%"), the methods and systems described herein produce outputs that can be interpreted by the clinical user (e.g., the system outputs: "The iliac bone does not appear horizontal", or "The left ventricle is not fully visible"). The workflow 400 is then repeated through the step 402.

In some embodiments, guidance provided in the step 420 includes retrieving an atlas of anatomical structures of interest. In some embodiments, the atlas can include a 3D model of an anatomical structure of interest, such as the 3D model 530 in FIG. 5B. The atlas is used to determine image quality and/or provide guidance to improve image quality, in some embodiments. In some embodiments, given a 3D model of an anatomical structure of interest (e.g., 3D model 530) and an ultrasound image (e.g., image 538 in FIG. 5B), the computing device can determine (e.g., identify) (e.g., via an algorithm) an anatomical plane corresponding to an anatomical structure that is currently acquired by the ultrasound probe.

In some embodiments, the computing device determines an anatomical plane corresponding to an anatomical structure whose image is currently acquired by the ultrasound probe using a trained neural network. In some embodiments, the trained neural network is a trained CNN. In some embodiments, the trained neural network is configured to output a point in 6-dimensional space indicating three positional and three rotational degrees of from (e.g., x, y, and z coordinates and pitch, roll, and yaw angles) with respect to the 3D model of the anatomical structure of interest. In some embodiments, the trained neural network can output the angles of the imaging plane in the x-y, y-z, and x-z direction, as well as the distance of the plane to the origin of the 3D model.

In some embodiments, the trained neural network, instead of giving, as an output, a vector representing probabilities, provides values associated with a 6-dimensional vector as an output. In some embodiments, a loss function that is a weighted sum of squared errors or any other loss function suitable for real-valued vectors that are not constrained to be probabilities may also be provided as an output.

In some embodiments, the computing device determines an anatomical plane corresponding to an anatomical structure whose image is currently acquired by the ultrasound probe by partitioning the angle-distance space into discrete classes, and then using a trained neural network that outputs the class of the input image. In some embodiments, the computing device includes (or is communicatively connected with) a bank of images (e.g., a database of images, such as labeled images 392 in the database 380) that has been labeled with their relative positions. The computing device identifies an image in the bank of images that is "closest" to the input image. Here, closest refers to the minimum distance function between the input image and every other image in the bank.

In some embodiments, the computing device computes (e.g., measures) a respective distance between an acquired image in a probe-position space (e.g., a six-dimensional space indicating the (x, y, z) position and rotations in the x-, y-, and z-axis with respect to the 3D model of the anatomical structure of interest) and a predicted plane in a probe-position space that would provide a better image, and determines, based on the computation, a sequence of steps that will guide the user to acquire the better image. In some embodiments, the computing device causes the sequence of steps or instructions to be displayed on a display device that is communicatively connected with the ultrasound probe.

In some embodiments, instead of computing a distance between the current image in the probe-position space and a predicted plane, the computing device classifies the current image as one of n possible classes. In some embodiments, changing a tilt of an ultrasound probe can lead to different planes of an organ (e.g., the heart) to be imaged. Because the views of the anatomical planes are well-known in medical literature, a convolutional neural network can be used to train a classifier that identifies what a current view captured by the image acquired in the step 402 corresponds to.

In some embodiments, the computer system used to implement the workflow 400 may be a local computer system or a cloud-based computer system.

The methods and systems described herein do not assume or require an optimal image, or that an "optimal image" would be the same for every patient who is scanned by the ultrasound probe. The use of an "optimal image" also does not take into account differences in the anatomical positions of organs in different people, or provide any rationale why a big (or a small) deviation is observed in an input image. Thus, the methods and systems described herein do not include logging deviations between an input image and an optimal image. Nor do the methods and systems described herein involve training a predictor to estimate any such deviation. Instead, the methods and systems segment one or more relevant organs from the obtained images and provide, as an output of the predictor, a set of segmentation masks. The methods and systems described herein identify the respective location(s) of the organs in an image, and are thus robust against differences in the position of the organs across different people.

Instead of training a neural network based on a set of rules to obtain an output that quantifies a degree of confidence that a particular feature is absent or present in an input image, the methods and systems described herein leverage medical information to identify relevant anatomical structures in an input image. Such an approach eliminates the need for collecting a training set for training a neural network to quantify a degree of confidence. Further, instead of providing a degree of confidence regarding the presence of some landmarks, the methods and systems described herein are based on the identification of anatomical structures.

Instead of determining a quality of a particular ultrasound image acquired in the step 402 by an output of a neural network, which may implicate the issue of non-calibration present in neural networks, the methods and systems described herein additionally use probabilistic methods. In some embodiments, calibrated systems provide outputs that correspond to real probabilities. Usually, neural networks that work with imaging data perform two tasks: (1) estimate the probability of an event by finding patterns in the training examples and (2) finding a mapping between the training instances to the estimated probabilities. Estimating the probabilities based on the analysis of pixels alone (as traditional methods may do) requires hundreds of thousands of images, which are often unavailable. Instead, it is possible to directly provide such probabilities during the training procedure by using probabilistic labels instead of categorical ones. Therefore, in some embodiments, the process may involve networks finding the mapping between input images and probabilities, using several orders of magnitude less data to accomplish the objective. In a nonlimiting example of diagnosing hip dysplasia, the angle between the acetabular angle and the coverage of the femoral head provide an indication of the likelihood of the condition. Such an approach may allow much less data to be used in training before a calibrated output is generated by the system.

FIG. 6 illustrates an example of a multitask approach for encoding domain specific knowledge into a machine learning algorithm, in accordance with some embodiments. A workflow 600 for segmenting anatomical parts of interest in an acquired image is shown in FIG. 6. In some embodiments, the acquired image has undergone style-removal and has been mapped into a common space (e.g., common space 560, as shown in FIG. 5A). The example illustrated in FIG. 6 shows a schematic thyroid ultrasound image 602. In some embodiments, an output of the workflow 600 provides (e.g., automatically, or without user input) a mask 606 that identifies an attribute of interest (e.g., an anomaly, a tumor) in a body region (e.g., an organ, the thyroid) using a machine learning algorithm 604. In some embodiments, instead of the mask 606 that identifies a particular anatomical region of interest (e.g., a mask that solely identifies a single anatomical region of interest), the workflow 600 additionally or alternatively provides the machine learning algorithm 604 as a multitask learning algorithm. The multitask learning algorithm uses medical expert knowledge 610 to define a new mask 612 that contains other relevant anatomical structures including structures 608, 614, 616, and 618, that are not the anatomical regions of interest (e.g., tumors). In some embodiments, the multitask learning algorithm generates an output having multiple features (e.g., not an output that provides a single determination or feature). In some embodiments, the medical expert knowledge 610 is provided by a human expert manually annotating additional anatomical structures in a set of training images that are in the common space, and using the manually annotated training images to train the machine learning algorithm 604 to output the new mask 612. In some embodiments, the medical expert knowledge 610 is provided by a human expert manually annotating training sets that include a collection of new masks that include multiple relevant anatomical structures, in addition to the anatomical feature of interest. In some embodiments, the medical expert knowledge may be provided, via an atlas of anatomical structures or other medical literature, as information about spatial relationships between possible relevant anatomical structures. In some embodiments, the atlas includes a three-dimensional representation of the anatomical structure of interest (e.g., hip, heart, or lung).

In some embodiments, the machine learning algorithm 604 may include a classifier that identifies a current view associated with the image 602, and determine relevant anatomical structures likely to be associated with the current view. In some embodiments, this multitask approach allows the machine learning algorithm 604 to learn a better representation of the image 602 that may increase its performance.

Figure 7:
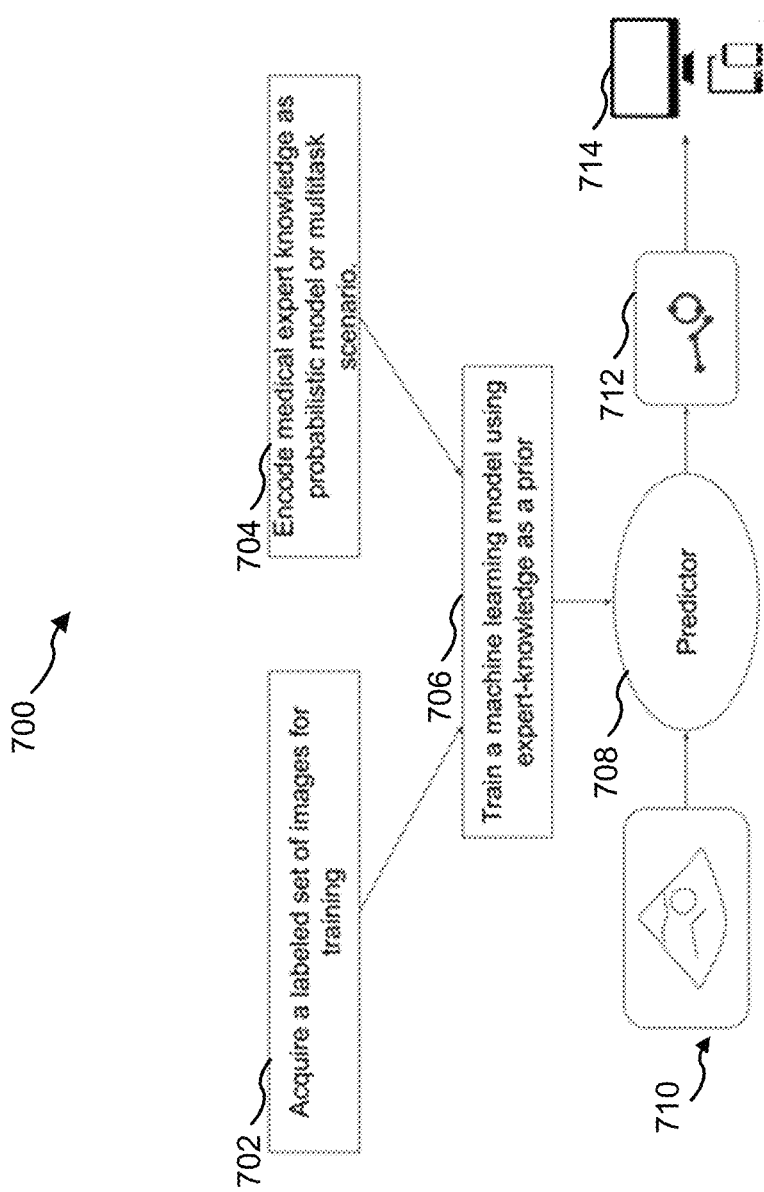
FIG. 7 illustrates an example of incorporating domain-specific knowledge into a machine learning model, in accordance with some embodiments.

FIG. 7 illustrates an example of incorporating domain-specific knowledge into a machine learning model, in accordance with some embodiments. A workflow 700 that includes training a machine learning model is shown in FIG. 7. A computer system receives (702), as an input, a labeled set of images for training. In some embodiments, the set of labeled images includes training images in which one or more (e.g., all) relevant anatomical structures present in the image are labeled. In some embodiments, the set of labeled images includes training images depicting one or more healthy anatomical structures and training images depicting one or more diseased anatomical structures. In some embodiments, in addition to identification information, respective anatomical structure are labeled with positional information (e.g., relative positional information, including angles relative to one or more reference planes or with respect another anatomical structure). In some embodiments, training images of a respective anatomical structure are labeled with quality information relating to how suitable a respective image is for diagnostic purposes) (e.g., a measure of how visible a femoral head is, a measure of how horizontal a line corresponding to the ilium is). In some embodiments, the quality information includes assigning a quality score to an ultrasound image. In some embodiments, assigning the quality score occurs automatically in response to acquisition of the ultrasound image during the scan. In some embodiments, image quality is assessed one frame at a time. In some embodiments, image quality for a newly acquired image is assessed based on the newly acquired image, as well as a sequence of one or more images acquired right before the newly acquired image. The computer system also receives (704), as an input, encoded information that contains medical expert knowledge.

Typical machine learning models may receive a large amount of training data as input. In some embodiments, a smaller set of data (e.g., a much smaller set of data) is sufficient for training machine learning models when domain-expert knowledge (e.g., medical expert knowledge) is incorporated during the training. In some embodiments, domain-expert knowledge is encoded by providing target labels to training images. In some embodiments, using 200 images that incorporate domain-expert knowledge improves an accuracy of the output by an additional 15% (e.g., from 70% to 85%) compared to a neural network model trained using 200 images that do not incorporate domain-expert knowledge. For example, a medical expert manually annotates a set of training images for relevant anatomical structures (e.g., all relevant anatomical structures) present in the training images. In some embodiments, domain-expert knowledge is encoded using multi-task approaches. For example, when multiple anatomically relevant structures are annotated in each of a number of training images, the multitask approach allows probability distributions for respective anatomically relevant structures appearing together to be determined. In some embodiments, the multitask approach allows the network to learn additional patterns sets. For example, training the model using the label "tumor" vs. the label "non-tumor," may cause the system to treat all "non-tumor" regions or segments similarly, without distinction. This may not be the correct approach most of the time, since there might be other elements in the image that are very different from one another (liver, kidney, diaphragm, etc.) In some embodiments, by providing additional labels (e.g., kidney, liver, or bladder) in the image that is not related to the feature of interest (e.g., tumor), the network is able to learn additional patterns that may improve its performance. By incorporating domain-expert knowledge in the training data, a novel way of learning the parameters of machine learning models provides comparable performance using a smaller set of training data vis-à-vis typical machine learning models.

Using the labeled set of images from the step 702, and the encoded medical expert knowledge from the step 704, the computer system trains (706) a machine learning model using the expert-knowledge as a prior. The output of the training from the step 706 produces a predictor that analyzes (708) an input image from an ultrasound probe that obtains (710) the input image. In some embodiments, the input image is processed to reduce or remove probe-specific effects, described above in reference to style removal, before it is provided as an input to the predictor in the step 708. The predictor automatically segments one or more anatomical features of interest and identifies (712) the relevant anatomical landmarks from the input image of the step 710. The computer system displays (714) the output from the step 712 either on a display of the computer system or it may be displayed on a local device (e.g., cell phone or tablet) of a medical provider and/or patient.

In general, machine learning leverages a stored dataset (e.g., the training dataset) extracted from a stored set of training images to automatically learn patterns from that set of stored images. Such a machine learning approach may be different from pattern recognition methodologies, in which the pattern to be recognized is predefined, and the pattern recognition module provided an output as to whether the predefined pattern is present or not in a particular input image (e.g., a test image, or an image to be processed). Using machine learning approaches, patterns can be extracted or learned without a need to predefine them. For example, probabilistic graphical models (PGMs) encode probability distributions over complex domains in which joint (multivariate) distributions involve large numbers of random variables that interact with one another.

In some embodiments, the workflow 400 is based on anatomical identification of structures of interest combined with priors obtained from medical experts and not based on tissue features. Traditional learning methods typically do not allow the incorporation of domain-expert knowledge. For example, the workflow 400 does not extract information exclusively from the training examples, in contrast to methods that are fully data driven. Methods that are fully data driven do not allow expert-domain knowledge (e.g., notes) to be incorporated into the training data set, since they are restricted to analyze patterns in data used as input to the system. In contrast, the workflow 400 combines medical-expertise with segmentation networks to map an image into a template (e.g., the step 418 in FIG. 4 and further described in FIG. 10), and then uses the relative location of the image with respect to the template to provide feedback to the user (e.g., the step 420 in FIG. 4).

The workflow 400 provides as output a series of characteristics of an image, leaving the final diagnosis to a medical expert. The workflow 400 does not require the position and orientation of the scanning device, eliminating the need for dedicated external sensors to measure these attributes.

The workflow 400 addresses domain adaptation to ensure a successful implementation of a quality detection tool. Images acquired with different probes produce images with different probability distributions. In order to successfully use any computer algorithm to automatically assess the quality of an image, workflow 400 maps the acquired images into a common space that is device agnostic. The workflow 400 also includes semantic image segmentation, which adapts to different variations in shape and positions of the anatomical structures of interest. The workflow 400 maps the segmented image to a 3D template to suggest a new positioning of the scanning device, while not requiring the position and orientation of the scanning device. The workflow 400 maps the ultrasound images to a 3D template, allowing movement to be directly computed in real time, without the need of storing precomputed movements of the ultrasound probe in a database.

In some embodiments, the workflow 400 focuses on the quality of an ultrasound image in a single view, and not with providing guidance to acquire images from different views. The workflow 400 does not require ultrasound images from different planes, or the use of an image from one plane as reference for the rest of the images taken in other planes.

The methods, systems, and devices described herein relate to an automated, device-agnostic method for analyzing an anatomical structure of interest in a follow up exam. In a follow up exam, an ultrasound image of an anatomical structure of interest (e.g. an abnormality in the body of a patient, an abnormality in an organ, or a nodule in the thyroid) is obtained, and then compared with a different (e.g., a second) image of the same anatomical structure of interest obtained at a different timepoint (e.g. a month ago, three months ago, one year ago). For making a meaningful comparison, images may be acquired to be as similar as possible in terms of probe position and orientation (e.g., probe angle). For example, in some embodiments, to compare sizes of anatomical features, a second image is obtained from approximately the same plane in a comparable view.

As information of the position and angle of the ultrasound probe is usually not available (e.g., as separately stored information associated with a particular acquired ultrasound image, or is not associated as metadata to the acquired ultrasound image), manually performing a follow up scan to track an anatomical structure of interest may be a challenging task. For example, a follow up scan may be conducted at a different medical facility by a different clinician using a different ultrasound system (e.g., manufactured by a different manufacturer, be a different model from the ultrasound system used to collect the first image). The methods, systems, and devices described herein relate to finding, characterizing, and comparing an anatomical structure of interest in two or more ultrasound images acquired at different timepoints. The images might be acquired by different specialists using different ultrasound probes and different configurations of the probe. In some embodiments, different configurations correspond to different sets of operating parameters (e.g., frequency, phase, duration, movement direction, and/or transducer array type) of the ultrasound probe and/or requirements (e.g., presence, positions, sizes, and/or spatial relationships of landmarks selected based on scan type, clarity of image, and/or other hidden requirements based on machine learning or other image quality scoring methods) on the ultrasound images.

Figure 8:
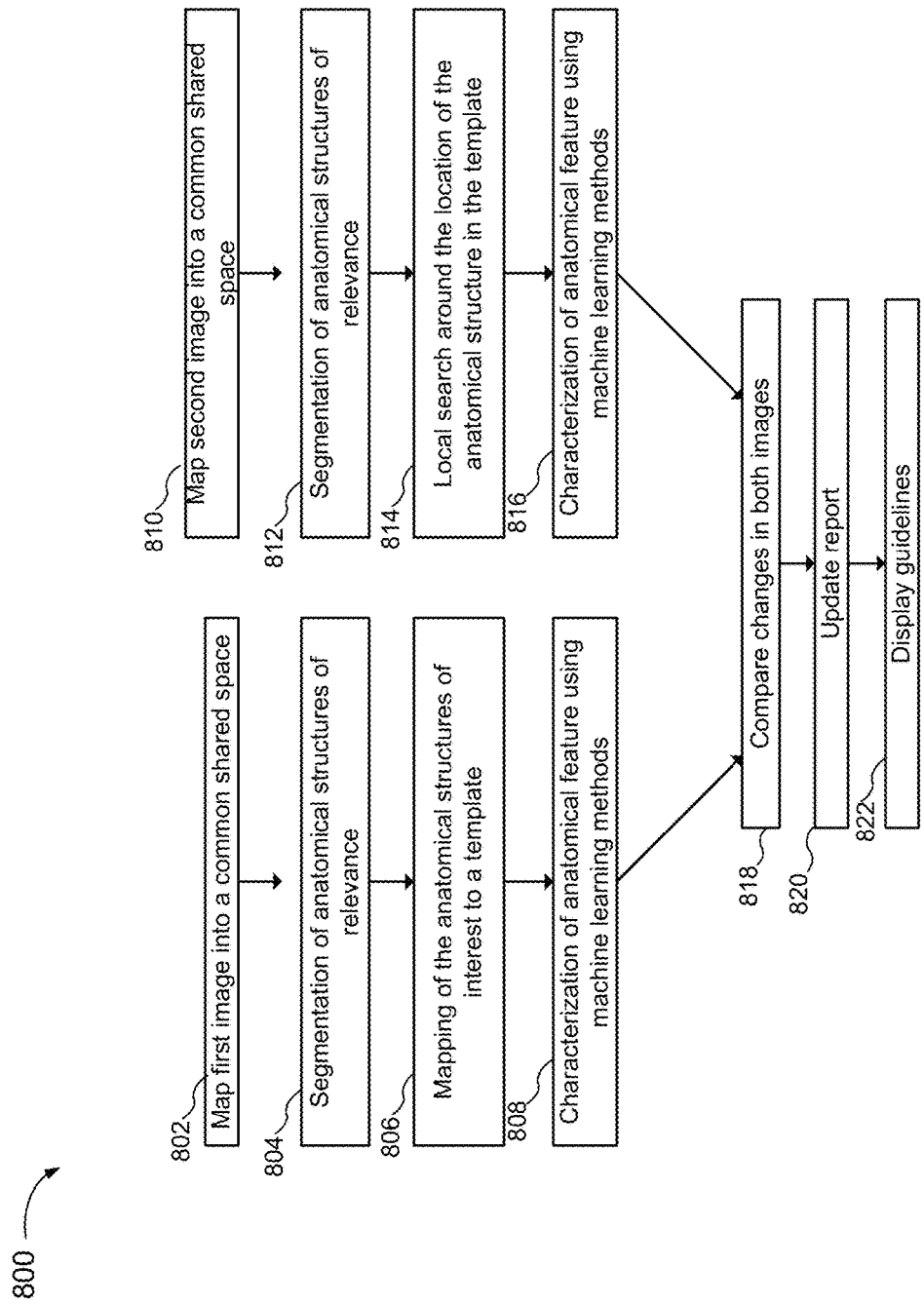
FIG. 8 is a workflow for performing a device-agnostic follow-up acquisition of ultrasound images, in accordance with some embodiments.

FIG. 8 illustrates a workflow 800 for automatically comparing two or more diagnostic images (e.g., ultrasound images) of an anatomical structure of interest taken at different points in time, in accordance with some embodiments. In some embodiments, the workflow 800 is performed by one or more processors (e.g., CPU(s) 302) of a computing device that is communicatively connected with an ultrasound probe. For example, in some embodiments, the computing device is a server or control console (e.g., a server, a standalone computer, a workstation, a smart phone, a tablet device, a medical system) that is in communication with the ultrasound probe. In some embodiments, the computing device is a control unit integrated into the ultrasound probe. In some embodiments, the ultrasound probe is a handheld ultrasound probe or an ultrasound scanning system.

A first ultrasound image is acquired using one or more of an ultrasound probe's acquisition modalities, including a single (e.g., static) 2D image, an automated sweep yielding a series of (static) images for different 2D planes (e.g., 2D sweep), a cine clip, which is a real time video capture of scanned anatomy, or a single scan that acquires a 3D volume of images corresponding to a number of different 2D planes (e.g., a 3D scan).

In some embodiments, the workflow 800 maps (802) a first ultrasound image that includes anatomical areas of interest into a common space that is device-agnostic, as described above in reference to workflow 400. Images acquired with different scanning devices, or with the same scanning device with different image acquisition parameters, might have a different quality. The mapping corrects for these differences so that differences in probability distribution of the images are reduced (e.g., the probability distribution of the images are substantially the same). The identification of anatomical structures of relevance may be done manually or automatically. In some embodiments, the process is done automatically via digital image processing or machine learning algorithms.

The workflow 800 segments (804) anatomical structures of relevance from the image that has been mapped into the common space. The segmented anatomical structure from the step 804 is mapped to a 3D template, as described above in reference to workflow 400. The segmentation in the step 804 may also be done on either the raw ultrasound image, or the ultrasound image that was mapped to the common shared space. In some embodiments, when the ultrasound image is used, the automatic segmentation algorithm is trained using domain adaptation techniques. In some embodiments, medical expert knowledge or information about the anatomy of the human body is incorporated to improve the quality of the segmentation. The segmentation algorithm might identify several anatomical structures that appear on the ultrasound image, even if not all the anatomical structures are analyzed in subsequent tasks (e.g., similar to the multitask scenario described in FIG. 6).

Figure 9:
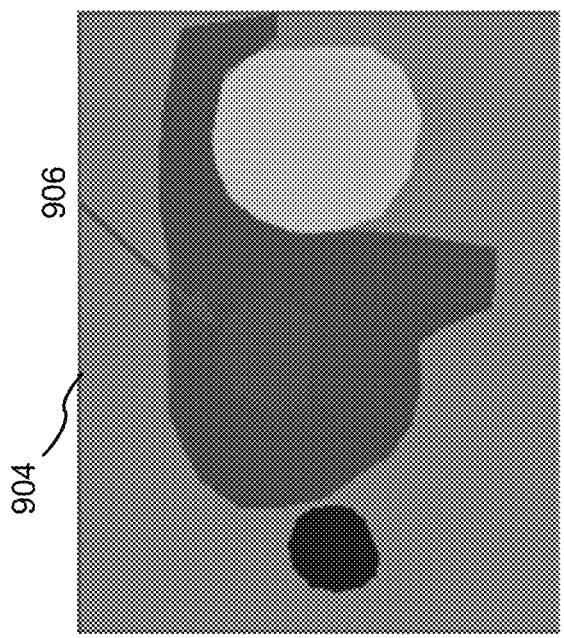
FIG. 9 illustrates an example input and an example output of a system that automatically identifies relevant structures of interest, in accordance with some embodiments.
Figure 9:
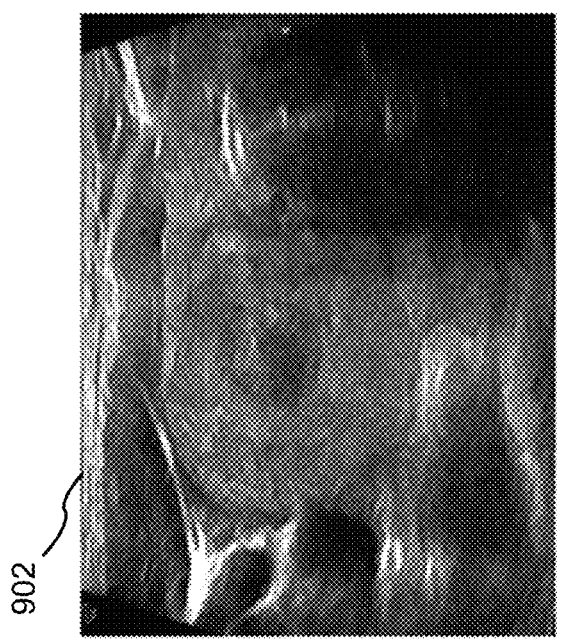

As illustrated in FIG. 9, an input image 902 obtained using an ultrasound probe is analyzed by a machine learning, computer vision, or image processing algorithm. An example of an output of the segmentation process outlined in the step 804 is a segmentation mask 904 that automatically identifies several anatomical structures that are visible on the input image 902. For example, the anatomical region of interest 906 is the one that will be characterized, while the rest of the anatomical structures might be used to map the region 906 to a template 1000 during a step 806, described below.

In some embodiments, an image segmentation algorithm with domain adaptation capabilities may provide good performance regardless of the ultrasound device used to acquire the image. Domain adaptation is the ability to apply an algorithm trained in one or more "source domains" to a different (but related) "target domain". Domain adaptation is a subcategory of transfer learning. In domain adaptation, the source and target domains all have the same feature space (but different distributions); in contrast, transfer learning includes cases where the target domain's feature space is different from the source feature space or spaces. In some embodiments, the feature space includes various characteristics of an anatomical structure of interest. The different distributions associated with the feature space could be due to probe-specific effects. In other words, the source domain may be a machine learning training trained using images obtained from a first ultrasound probe, and the target domain is for images obtained using a second ultrasound probe, different from the first ultrasound probe.

Figure 10:
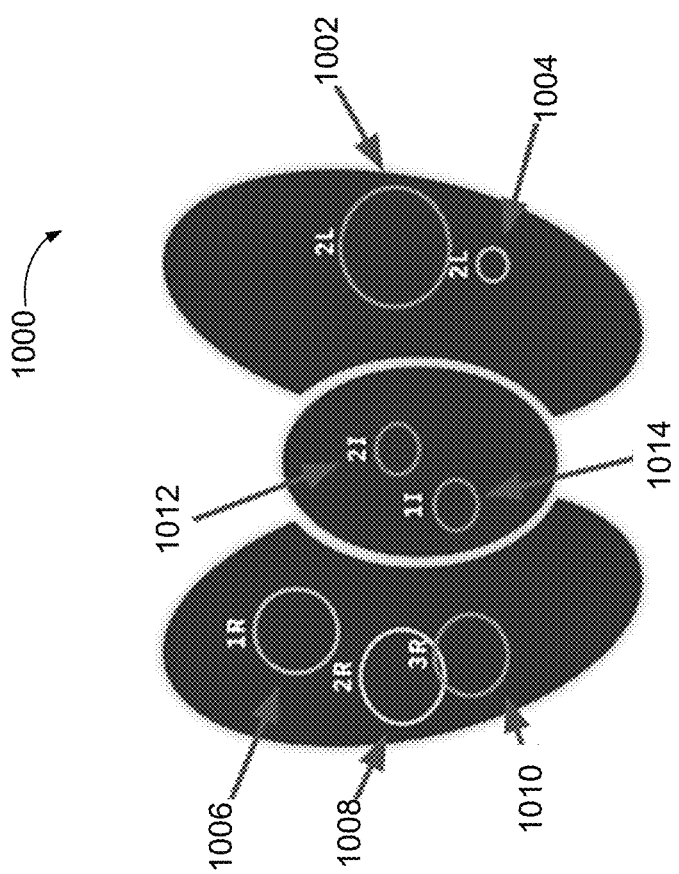
FIG. 10 illustrates an example process for mapping anatomical structures of interest to a template, in accordance with some embodiments.

The workflow 800 maps (806) anatomical structures of interest segmented from the step 804 into a template. As shown in FIG. 10, a location of the anatomical region of interest 906 is mapped into a common template 1000. The template 1000 has markers 1002, 1004, 1006, 1008, 1010, 1012, and 1014 at locations of the different anatomical regions. In some embodiments, the location includes a set of coordinates, or any other identifier that indicates a relative position of the anatomical region of interest 906 that appears on the image 902.

In some embodiments, after identifying the anatomical structure of interest, the workflow 800 includes storing location information of the structure by placing a marker on a template that represents the anatomy of an organ. In some embodiments, the template is a simplified representation of an organ (e.g., the thyroid gland), and the marker is a set of coordinates that indicate the location of the anatomical structure of interest (e.g., a thyroid nodule). In some embodiments, the location information of the anatomical structure of interest is used in subsequent follow-up exams (e.g., in a step 814, as explained below) to quickly identify the anatomical structure of interest in the later acquired images.

Figure 11:
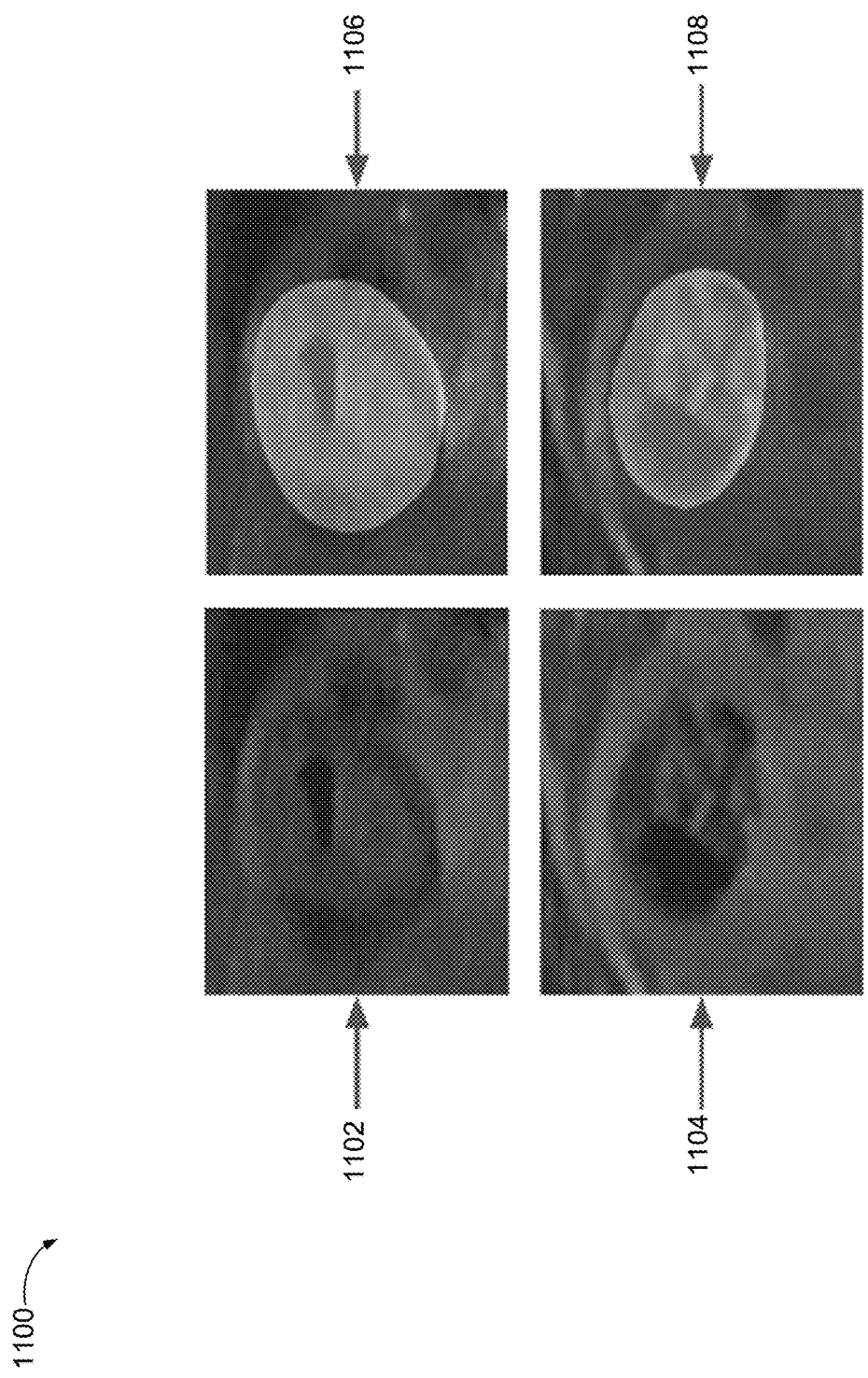
FIG. 11 shows an example for identifying an anatomical structure of interest, in accordance with some embodiments.

The workflow 800 characterizes (808) the anatomical feature using machine learning methods. In some embodiments, machine learning methods similar to those described in reference to the step 410 in FIG. 4 are used. In some embodiments, as shown in FIG. 11, the anatomical region of interest 906 is characterized by a set of clinically relevant features. For example, a clinician may first select the anatomical region of interest 906 from the image 902 to be analyzed. In some embodiments, the selection includes creating a first bounding box 1102 and a second bounding box 1104 around the structures to be analyzed. Then, the step 808 includes providing finer segmentation masks 1106 and 1108 of the anatomical structures of interest inside the bounding boxes 1102 and 1104.

Figure 12:
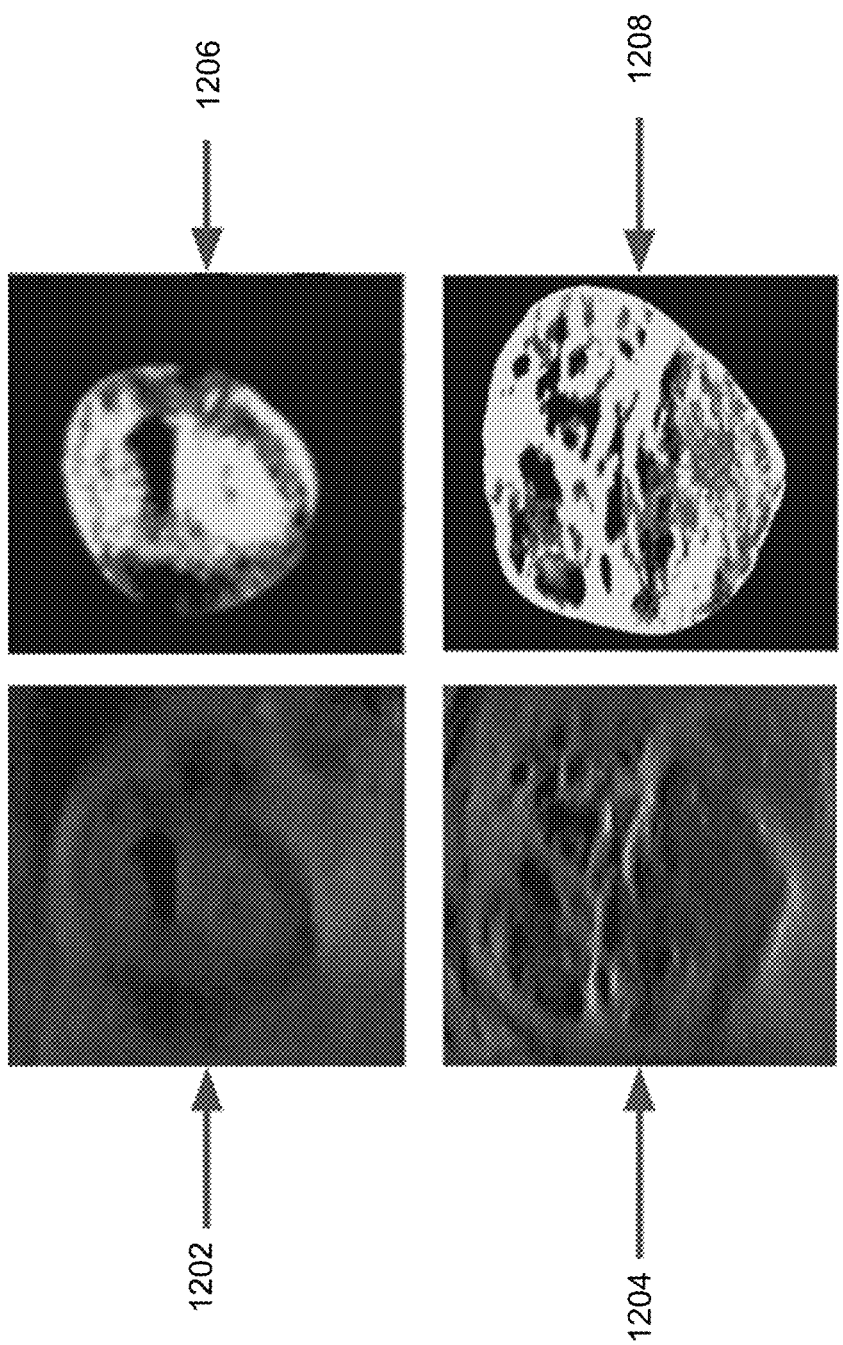
FIG. 12 shows an identification of solid and cystic parts inside a nodule of a thyroid, in accordance with some embodiments.

The step 808 also includes extracting a set of features that are clinically relevant and representative of the anatomical region of interest 906. FIG. 12 shows one possible feature that can be extracted. The step 808 includes selecting a first bounding box 1202 and a second bounding box 1204 for identifying a state of the anatomical region of interest 906 within the two bounding boxes. Refined segmentation masks corresponding to each of the first bounding box 1202 and the second bounding box 1204 identify solid and cystic (liquid) parts within the anatomical region of interest 906. Further statistics can also be extracted, such as the percentage of solid tissue inside the nodule, and/or the shape and size of the nodule.

After storing the location of the anatomical structure of interest, machine learning algorithms are used to extract a set of features from such anatomical structure of interest that are clinically relevant to provide a diagnosis. For example, in the analysis of thyroid nodules the workflow 800 may include computing the TIRADS score of the nodule. This score is computed by characterizing the composition, echogenicity, margin, size and echogenic foci of the nodule. Such characterization might be obtained by a combination of digital image processing, machine learning and/or computer vision algorithms. All the features that are relevant for the characterization of the anatomical structure of interest may also be stored on a local computer system or a cloud-based database for future use in a follow-up exam.

The steps 802, 804, 806, and 808 may be conducted within a first time range at a first medical facility by a first clinician using a first ultrasound system. In some embodiments, a second ultrasound image is acquired in a second time range, separated from the first time range (e.g., the second time range is one month later than the first time range, the second time range is three months later than the first time range, the second time range is six months later than the first time range, or the second time range is a year or more later than the first time range).

During a follow-up exam, a new image of the anatomical region of interest is acquired. The workflow 800 maps (810) the second image into the common shared space. The workflow 800 then segments (812) anatomical structures of relevance from the second image. Thereafter, the workflow 800 locally searches (814) around the location of the anatomical structure in the template as determined in the step 806. In some embodiments, the workflow 800 segments the anatomical structure of interest by performing a local search in a window centered at the coordinates of the anatomical structure of interest derived from the first ultrasound image of the first exam. This segmentation process might be performed either manually or automatically by a segmentation algorithm. For example, using the markers 1002, 1004, 1006, 1008, 1010, 1012 and 1014, on the template 1000 (FIG. 10), the step 814 includes a local search for the anatomical region of interest 906 on the second image (e.g., the new image acquired within the second time range). In some embodiments, a clinician selects a bounding box around an anatomical structure of interest in a window centered around one or more of markers 1002, 1004, 1006, 1008, 1010, 1012, and 1014.

Based on the search results from the step 814, the workflow 800 characterizes (816) the anatomical features using machine learning methods. In some embodiments, once the anatomical structure of interest is segmented in the second image, the anatomical structure of interest is characterized using the same set of features used to characterize the anatomical structure of interest from the first image.

The steps 810, 812, 814 and 816 maybe conducted within a second time range different from the first time point at a different medical facility by a different clinician using a different ultrasound system.

The workflow 800 then compares (818) changes between the first image and the second image based on information characterizing the anatomical features from the step 808 and from the step 816 and in both images 818. In some embodiments, based on the outcome of the comparison from the step 818, workflow 800 also highlights and displays to the clinician differences across features extracted from the first image and the second image.

The workflow 800 updates (820) a report and displays (822) guidelines relevant to the medical condition implicated in the two acquired images. For example, the guidelines may be up-to-date official clinical guidelines to determine possible next steps. If the next step includes another follow-up scan, the workflow 800 also stores information relevant for performing data analysis in the future (e.g., information regarding operational parameters of the ultrasound probe (intensity, amplitude, frequency) and/or information about positioning of the ultrasound probe). In some embodiments, workflow 800 includes generating or updating a report indicating clinically-relevant differences between the characteristics of the object of interest identified on the original and on the follow up scan. For example, the comparison may include changes in size of the anatomical structure of interest, categories, or any other clinical feature of relevance.

In some embodiments, the workflow 800 is not based on a convolutional neural network, but uses probabilistic graphical models, image processing and machine learning methods to predict TIRADS grading. In some embodiments, the workflow 800 includes using a U-Net that produces a rough estimate of the boundaries of anatomical structures of interest (e.g., nodule) instead of using segmentation schemes (e.g., a nodule segmentation) that is based on ellipse fitting.

The workflow 800 includes tracking changes (or lack thereof) in an anatomical region of interest over longer periods of time compared to the tracking of the anatomical object of interest in real time, or near-real time during a medical procedure (e.g. radiotherapy). For the latter, real-time changes in the position, orientation, and features of the anatomical region of interest are relatively small and may typically be known, at least by the clinician who is performing the ultrasound scan. For comparing changes over longer periods of time, many factors may change significantly, such as the hardware used to track the anatomical region of interest, the position of the patient, the orientation and position of the probe. Most of the information regarding the protocol of image acquisition for the first image may be unknown when the subsequent images are acquired at a later time, which may make the acquisition task more difficult.

The workflow 800 can be used for the detection of bones and also for soft tissues. The workflow 800 can perform the difference analysis (e.g., between the image taken originally at an earlier time point with an image taken at a later follow-up scan) automatically for diagnostic purposes, without direct user input or intervention (e.g., without having to be manually analyzed by a clinician). In some embodiments, the workflow 800 is not aimed at visualizing images taken at different timepoints. In some embodiments, the workflow 800 does not include a registration step for the images acquired at two different points in time. The registration step may be highly difficult for ultrasound images because ultrasound images can be taken from different angles and positions, such that a correspondence between the two images may not exist. The workflow 800 circumvents this issue by not including a registration step and instead maps the anatomical features of interest into a common space (e.g., the step 806 in FIG. 8) that indicates the anatomical region where the object or structure of interest is located. In other words, mapping both ultrasound images to a common coordinate space, without expressly registering the images (e.g., without comparing one image to another, and determining a coordinate transformation based on said comparison), allows the approximate location of the anatomical structures of interest to be determined even if the ultrasound images are not fully aligned.

In some embodiments, the workflow 800 extracts features from the acquired ultrasound images and then compares the images in the feature space, avoiding the need of storing, rendering and overlaying the images. For example, the workflow 800 does not include performing a 3D rendering of an anatomical structure of interest (e.g., a tumor), and then overlaying the two rendered lesions or regions of interest to make a comparison. The workflow 800 includes mapping the ultrasound images into a feature space, computing a set of metrics in that new space, before comparing features extracted in the feature space. Thus, in some embodiments, the workflow 800 does not measure differences in volume in anatomical structures of features directly in the image space. Rather, the workflow 800 characterizes the objects (or anatomical structures) of interest by a set of measurements (e.g., categories of TIRADS scores) and then displays the changes of such measurements between the two timepoints or time ranges. The workflow 800 does not need to have access to both ultrasound images to make the comparison, since this process can be done independently for each image and the workflow 800 compares the extracted features.

In some embodiments, the workflow 800 independently identifies the anatomical regions of interest in the set of images taken at the first time range and the set of images taken at the second time range, instead of segmenting the anatomical region of interest in the second set of images (obtained during the later time range) based on the segmentation of the first set of images (obtained during the earlier time range).

The workflow 800 addresses the problem of domain adaptation, which makes images acquired under different protocols or with different hardware, potentially incompatible. In some embodiments, the workflow 800 also eliminates the need for detecting landmarks and reference points to make a comparison between the anatomical object of interest at two different timepoints.

FIGS. 13A-13C illustrate a flowchart diagram for a method 1300 of guiding an ultrasound probe (e.g., to achieve diagnostic objectives of tracking a structure overtime, an anatomical structure, an imaging artifact associated with an anatomical structure of ultrasound imaging using an ultrasound probe), in accordance with some embodiments. In some embodiments, the ultrasound probe (e.g., ultrasound device 200) is a handheld ultrasound probe, or an ultrasound scanner with an automatic probe. In some embodiments, the method 1300 is performed at a computing device (e.g., computing device 130 or computing device 300) that includes one or more processors (e.g., CPU(s) 302) and memory (e.g., memory 306). For example, in some embodiments, the computing device is a server or control console (e.g., a server, a standalone computer, a workstation, a smart phone, a tablet device, a medical system) that is in communication with a handheld ultrasound probe or ultrasound scanning system. In some embodiments, the computing device is a control unit integrated into a handheld ultrasound probe or ultrasound scanning system.

At a computer system that includes one or more processors and memory, and optionally, an ultrasound device, the computer system obtains (1302) a first frame of a probed region acquired using a first probe device at a first time, and a first set of control parameters used to acquire the first frame. The computer system processes (1304) the first frame (e.g., the first frame is an image frame selected from a first plurality of image frames corresponding to different planes within a measurement volume; the measurement volume is obtained in a single scan; in some embodiments, machine learning (ML) is used to select the first frame from the plurality of image frames) to obtain a first set of attributes. In some embodiments, the term "attributes" as used herein broadly encompasses characteristics related to "features" and also "structure," for example, brightness, image quality and other parameters related to image acquisition. In some embodiments, an attribute of a first image refers to a feature or signal that appears in the first image, or may refer to attributes of an anatomical structure. Features may refer to an aspect of the content image, e.g., that can be segmented from other content of the first frame. In some embodiments, processing the first frame includes segmenting one or more features (e.g., the one or more attributes includes a size of the feature, characteristics of the feature; whether the feature is solid or liquid; geometric arrangement near the feature) from the first frame after one or more first probe-specific effects are reduced in the first frame based at least in part on the first set of control parameters. Processing the first frame can include: running feature extractions; resizing pixels, eliminating noise profile specific to a probe device; and rescaling a magnitude of a value associated with a pixel (e.g. including determining the rescaled value by machine learning).

In accordance with a determination that the first frame contains a respective attribute present in a second frame acquired at a time earlier than the first time using a second set of control parameters: the computer system displays (1318), on a user interface, information related to differences in the respective attribute based on the first frame and the second frame. In some embodiments, the respective attribute corresponds to an anatomical structure or artifact. In some embodiments, multiple anatomical structures are used for multitasking machine learning processes. For example, the information relates to changes of the structure (e.g., changes in a size of the structure, a position of the structure, and/or a number of structures) between the first time and the earlier time. The information may also include displaying additional medical information based on the changes. In some embodiments, the medical information includes clinical guidelines with a recommended course of action to take based on the changes. In some embodiments, the second set of control parameters is the same as the respective set of control parameters used to acquire the first frame. In some embodiments, the second set of control parameters is different from the respective set of control parameters used to acquire the first frame.

The second frame is obtained by processing the one or more features segmented from the second frame after one or more second probe-specific effects are reduced in the second frame. For example reducing the second probe-specific effects includes eliminating second probe specific effects. The probe-specific effects are reduced by mapping the first frame into a common shared space; running feature extractions; resizing pixels; and/or eliminating noise profile specific to the second probe device. In some embodiments, eliminating the noise profile includes rescaling a magnitude of the pixel value and a range of the rescaling is determined by a machine learning algorithm.

In some embodiments, reducing the one or more first probe-specific effects in the first frame includes one or more elements selected from a group consisting of: preprocessing (1306) the first frame to account for the first set of control parameters and the second set of control parameters, and removing noise from the first frame.

In some embodiments, preprocessing the first frame to account for the first set of control parameters includes resizing (1308) pixels in the first frame, and removing noise from the first frame includes subtracting noise from the first frame using a noise profile specific to the first probe device, and rescaling a magnitude of values associated with respective pixels in the first frame.

In some embodiments, rescaling the magnitude of the values associated with the respective pixels to a rescaled range includes using machine learning to dynamically (e.g., after the acquisition of each additional frame) determine (1310) the rescaled range. In some embodiments, a machine learning model is trained using a lower resolution and/or otherwise de-noised device-agnostic frames.

In some embodiments, segmenting the one or more features from the first frame includes segmenting (1312) the one or more features from the first frame using one or more spatial locations derived from the second frame. In some embodiments, segmenting the first frame into the one or more features based on the spatial locations derived from the second frame includes obtaining (1314) the spatial locations from the template. The method further includes performing a local search in a window centered at coordinates corresponding to the spatial locations. For example, the coordinates of the one or more features are coordinates in the common shared space and a subset of segmentation results of the second modified frame includes the one or more features.

In some embodiments, displaying the information related to differences in the structure includes displaying (1320) information about changes to the one or more segmented features (e.g., movement, morphing, changes exceeding a predefined change in size) that are clinically relevant.

In some embodiments, processing the one or more features segmented from the second frame includes mapping (1322) the one or more features onto a template. In some embodiments, mapping the one or more features into the template includes mapping the first/second frame into a common shared space. In some embodiments, the template includes a 3-dimensional anatomical model. In some embodiments, the template is an array of feature characteristics, each with respective values, and the template is not a 3D anatomical model.

In some embodiments, the template includes one or more markers that identify (1324) locations of one or more anatomical regions of interest, the one or more anatomical regions of interest include a first anatomical region of interest in which the respective attribute is located. The location may include a set of coordinates, or any other identifier that indicates the relative position of the anatomical region of interest within an acquired image.

In some embodiments, the second frame is acquired (1316) using a second probe device different from the first probe device. In some embodiments, a second probe device is a different from the first probe device when it has a different model or is made by a different manufacturer, has a different hardware configuration, or has a different set of control parameters. In some embodiments, images acquired with different probes or with different settings have a different appearance. In some embodiments, the images generated by different probes, or different configurations of a probe, are samples from a different probability distribution over the intensity of the pixels/voxels.

In some embodiments, the computer system further includes in accordance with a determination that the first frame fails to meet a first criteria related to an anatomical region of interest (e.g., first criteria are domain-specific requirements provided via annotated training image sets that include boundaries of anatomical regions of interest): providing (1326) guidance (e.g., displaying on the user interface, or providing audio guidance feedback) for positioning the first probe device at a different location from a location where the first frame was acquired. For example, the different location has the same x, y, z coordinates but different rotational angles to obtain a third frame of a structure within the anatomical region of interest, the third frame having a higher image quality metric compared to the first frame. In some embodiments, the image quality metric is indicative of how close the obtained frame corresponds to a desired image plane of an anatomical region of interest of the structure.

In some embodiments, the computer system further generates (1328) a statistical model based on the one or more features to determine a presence of an anatomical region of interest in the first frame. For example, the structure is in the anatomical region of interest; the one or more features include anatomically relevant landmarks. In some embodiments, landmarks are used as priors in a statistical shape model to refine the boundaries of the anatomical regions of interest.

In some embodiments, the computer system further includes: in accordance with a determination that the first criteria related to the anatomical region of interest have been met, compute (1330) a metric of interest associated with the structure. In some embodiments, a metric of interest relates to dimensions of the structure, metric of interest relates to an angle associated with the structure (or between the structure and another element). In some embodiments, the method further includes displaying the computed metric of interest.

In some embodiments, the computer system further processes (1332) the third frame by segmenting one or more features from the third frame after one or more probe-specific effects are reduced in the third frame, and displaying, on the user interface, information related to differences in the structure based on the third frame and the second frame. In some embodiments, the third frame is obtained from approximately a same plane and/or in a comparable field of view as the second frame (correspond to one or more anatomical planes that match a desired anatomical plane of a target anatomical structure).

In some embodiments, the one of more features segmented from the first image includes (1336) features that are invariant to the first probe device.

In some embodiments, the first frame is obtained by selecting (1338) a frame from a plurality of frames acquired in a sweep. In some embodiments, the computer system further obtains (1340) a second frame of the probed region acquired using a second probe device, and a second set of control parameters used to acquire the second frame; and processes the second frame to obtain a second set of attributes of the second frame. In some embodiments, processing the second frame includes segmenting one or more features from the second frame after one or more second probe-specific effects are reduced in the second frame based at least in part on the second set of control parameters.

FIG. 14 illustrates a flowchart diagram for a method 1400 of guiding an ultrasound probe (e.g., to achieve diagnostic objectives of tracking a structure over time, an anatomical structure, an imaging artifact associated with an anatomical structure of ultrasound imaging using an ultrasound probe), in accordance with some embodiments. In some embodiments, the ultrasound probe (e.g., ultrasound device 200) is a handheld ultrasound probe, or an ultrasound scanner with an automatic probe. In some embodiments, the method 1400 is performed at a computing device (e.g., computing device 130 or computing device 300) that includes one or more processors (e.g., CPU(s) 302) and memory (e.g., memory 306). For example, in some embodiments, the computing device is a server or control console (e.g., a server, a standalone computer, a workstation, a smart phone, a tablet device, a medical system) that is in communication with a handheld ultrasound probe or ultrasound scanning system. In some embodiments, the computing device is a control unit integrated into a handheld ultrasound probe or ultrasound scanning system.

At a computer system that includes one or more processors and memory, and optionally, an ultrasound device, the computer system displays (1402) a user interface for presenting an analysis of a second frame of a structure obtained using a second probe device. For example, the second frame is an image frame selected from a second plurality of image frames corresponding to different planes within the measurement volume. In some embodiments, the measurement volume is obtained by a single scan. In some embodiments, machine learning is used to select the second frame from the plurality of image frames, the second frame has a highest quality metric associated with the structure. In some embodiments, the second probe device is the same as the first probe device. In some embodiments, the second probe device is different from the first probe device. In some embodiments, the second frame of the structure is obtained at a second time after a first frame of the respective attribute. For example, the first frame is an image frame selected from a first plurality of image frames corresponding to different planes within a measurement volume. In some embodiments, the measurement volume is obtained by a single scan. In some embodiments, a machine learning algorithm is used to select the first frame from the plurality of image frames, the first frame has a highest quality metric associated with the structure. In some embodiments, the first frame is obtained at a first time using a first probe device. In some embodiments, the first probe device is the same as the second probe device. In some embodiments, the first probe device is different from the second probe device.

The computer system displays (1404), on the user interface, information related to differences in the structure based on the first frame and the second frame, wherein the differences are characterized by processing one or more features segmented from the second frame after one or more probe-specific effects are reduced in the second frame and using one or more spatial locations derived from the first frame.

In one aspect, an electronic device includes one or more processors; and memory storing instructions that, when executed by the one or more processors, cause the electronic device to perform the method described above in reference to FIGS. 13A-13C and FIG. 14.

In another aspect, a non-transitory computer-readable storage medium having stored thereon program code instructions that, when executed by a processor, cause the processor to perform the method described above in reference to FIGS. 13A-13C and FIG. 14.

In another aspect, an electronic device, includes an input unit configured to receive a first frame of a probed region acquired using a first probe device having a plurality of transducers and a first set of control parameters used to acquire the first frame. In some embodiments, the first probe device is a handheld ultrasound probe, ultrasound scanner, the ultrasound probe is communicatively connected to the electronic device. The electronic device includes a memory unit configured to store data associated with a second frame acquired using a second set of control parameters. The electronic device includes a processing unit (e.g., the processing unit includes one or more processors and memory, control circuitry, ASICs, and/or other electrical and semiconductor controllers) configured to obtain or more attributes of the first frame, and to segment one or more features from the first frame after one or more probe-specific effects are reduced in the first frame based at least in part on the first set of control parameters, the processing unit is further configured to processing the one or more features segmented from the second frame after one or more probe-specific effects are reduced in the second frame to obtain information related to differences in a structure recorded in the first frame and the second frame; and a user interface configured to display the information related to the differences in the structure.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

It will also be understood that, although the terms first, second, etc. are, in some instances, used herein to describe various elements, these elements should not be limited by these terms. These terms are only used to distinguish one element from another. For example, a first transducer could be termed a second transducer, and, similarly, a second transducer could be termed a first transducer, without departing from the scope of the various described implementations. The first sensor and the second sensor are both sensors, but they are not the same type of sensor.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

What is claimed is:

1. A method, comprising:
at a computer system that includes one or more processors and memory:
obtaining a first frame of a probed region acquired using a first probe device at a first time, and a first set of control parameters used to acquire the first frame;
processing the first frame to obtain a first set of attributes of the first frame, wherein processing the first frame includes segmenting one or more features from the first frame after one or more first probe-specific effects are reduced in the first frame based at least in part on the first set of control parameters;
in accordance with a determination that the first frame contains a respective attribute present in a second frame acquired at a time earlier than the first time using a second set of control parameters:
displaying, on a user interface, information related to differences in the respective attribute based on the first frame and the second frame, wherein the second frame is obtained by processing the one or more features segmented from the second frame after one or more second probe-specific effects are reduced in the second frame.

2. The method of claim 1, wherein reducing the one or more first probe-specific effects in the first frame comprises one or more elements selected from the group consisting of: preprocessing the first frame to account for the first set of control parameters and the second set of control parameters, and removing noise from the first frame.

3. The method of claim 2, wherein preprocessing the first frame to account for the first set of control parameters comprises resizing pixels in the first frame, and removing noise from the first frame comprises subtracting noise from the first frame using a noise profile specific to the first probe device, and rescaling a magnitude of values associated with respective pixels in the first frame.

4. The method of claim 3, wherein rescaling the magnitude of the values associated with the respective pixels to a rescaled range comprises using machine learning to dynamically determine the rescaled range.

5. The method of claim 1, wherein segmenting the one or more features from the first frame comprises segmenting the one or more features from the first frame using one or more spatial locations derived from the second frame.

6. The method of claim 5, wherein segmenting the first frame into the one or more features based on the spatial locations derived from the second frame includes obtaining the spatial locations from a template, and the method further includes performing a local search in a window centered at coordinates corresponding to the spatial locations.

7. The method of claim 1, wherein displaying the information related to differences in the respective attribute includes displaying information about changes to the one or more segmented features that are clinically relevant.

8. The method of claim 1, wherein processing the one or more features segmented from the second frame comprises mapping the one or more features onto a template.

9. The method of claim 8, wherein the template includes one or more markers that identify locations of one or more anatomical regions of interest, the one or more anatomical regions of interest include a first anatomical region of interest in which the respective attribute is located.

10. The method of claim 1, wherein the second frame is acquired using a second probe device different from the first probe device.

11. The method of claim 1, further comprising:
in accordance with a determination that the first frame fails to meet a first criteria related to an anatomical region of interest:
providing guidance for positioning the first probe device at a different location from a location where the first frame was acquired to obtain a third frame of a structure within the anatomical region of interest, the third frame having a higher image quality metric compared to the first frame.

12. The method of claim 11, further comprising: generating a statistical model based on the one or more features to determine a presence of an anatomical region of interest in the first frame.

13. The method of claim 11, further comprising: in accordance with a determination that the first criteria related to the anatomical region of interest have been met, computing a metric of interest associated with the structure.

14. The method of claim 11, further comprising: processing the third frame by segmenting one or more features from the third frame after one or more probe-specific effects are reduced in the third frame, and displaying, on the user interface, information related to differences in the structure based on the third frame and the second frame.

15. The method of claim 14, wherein the third frame is obtained from approximately a same plane and/or in a comparable field of view as the second frame.

16. The method of claim 1, wherein the one or more features segmented from the first frame comprise features that are invariant to the first probe device.

17. The method of claim 1, wherein the first frame is obtained by selecting a frame from a plurality of frames acquired in a sweep.

18. The method of claim 1, further comprising:
obtaining the second frame of the probed region acquired using a second probe device, and the second set of control parameters used to acquire the second frame; and
processing the second frame to obtain a second set of attributes of the second frame, wherein processing the second frame includes segmenting one or more features from the second frame after one or more second probe-specific effects are reduced in the second frame based at least in part on the second set of control parameters.

19. A non-transitory computer-readable storage medium having stored thereon program code instructions that, when executed by a processor, cause the processor to perform operations comprising:
obtaining a first frame of a probed region acquired using a first probe device at a first time, and a first set of control parameters used to acquire the first frame;
processing the first frame to obtain a first set of attributes of the first frame, wherein processing the first frame includes segmenting one or more features from the first frame after one or more first probe-specific effects are reduced in the first frame based at least in part on the first set of control parameters;
in accordance with a determination that the first frame contains a respective attribute present in a second frame acquired at a time earlier than the first time using a second set of control parameters:
displaying, on a user interface, information related to differences in the respective attribute based on the first frame and the second frame, wherein the second frame is obtained by processing the one or more features segmented from the second frame after one or more second probe-specific effects are reduced in the second frame.

20. A computer system, comprising:
one or more processors; and
memory storing one or more programs, the one or more programs comprising instructions that, when executed by the one or more processors, cause the one or more processors to perform operations comprising:
obtaining a first frame of a probed region acquired using a first probe device at a first time, and a first set of control parameters used to acquire the first frame;
processing the first frame to obtain a first set of attributes of the first frame, wherein processing the first frame includes segmenting one or more features from the first frame after one or more first probe-specific effects are reduced in the first frame based at least in part on the first set of control parameters;
in accordance with a determination that the first frame contains a respective attribute present in a second frame acquired at a time earlier than the first time using a second set of control parameters:
displaying, on a user interface, information related to differences in the respective attribute based on the first frame and the second frame, wherein the second frame is obtained by processing the one or more features segmented from the second frame after one or more second probe-specific effects are reduced in the second frame.

* * * * *